(12) United States Patent
Dodge, II et al.

(10) Patent No.: US 7,935,860 B2
(45) Date of Patent: May 3, 2011

(54) ABSORBENT ARTICLES COMPRISING HIGH PERMEABILITY SUPERABSORBENT POLYMER COMPOSITIONS

(75) Inventors: Richard N. Dodge, II, Appleton, WI (US); Tammy J. Nettekoven, Neenah, WI (US); Scott J. Smith, Greensboro, NC (US); Stan McIntosh, Greensboro, NC (US); David L. Bergman, Jr., Greensboro, NC (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1044 days.

(21) Appl. No.: 11/728,243

(22) Filed: Mar. 23, 2007

(65) Prior Publication Data

US 2008/0234645 A1    Sep. 25, 2008

(51) Int. Cl.
*A61F 13/15* (2006.01)

(52) U.S. Cl. ......... 604/367; 604/366; 604/368; 604/370

(58) Field of Classification Search ................... 604/367, 604/366, 368, 370
See application file for complete search history.

(56) References Cited

U.S. PATENT DOCUMENTS

| | | |
|---|---|---|
| 3,783,871 A | 1/1974 | Sabee |
| 3,849,241 A | 11/1974 | Butin et al. |
| 4,036,233 A | 7/1977 | Kozak |
| 4,076,663 A | 2/1978 | Masuda et al. |
| 4,100,324 A | 7/1978 | Anderson et al. |
| 4,286,082 A | 8/1981 | Tsubakimoto et al. |
| 4,340,706 A | 7/1982 | Obayashi et al. |
| 4,497,930 A | 2/1985 | Yamasaki et al. |
| 4,500,315 A | 2/1985 | Pieniak et al. |
| 4,507,438 A | 3/1985 | Obayashi et al. |
| 4,587,154 A | 5/1986 | Hotchkiss et al. |
| 4,604,313 A | 8/1986 | McFarland et al. |
| 4,654,039 A | 3/1987 | Brandt et al. |
| 4,655,757 A | 4/1987 | McFarland et al. |
| 4,666,975 A | 5/1987 | Yamasaki et al. |
| 4,681,580 A | 7/1987 | Reising et al. |
| 4,683,274 A | 7/1987 | Nakamura et al. |
| 4,685,909 A | 8/1987 | Berg et al. |
| 4,724,114 A | 2/1988 | McFarland et al. |
| 4,734,478 A | 3/1988 | Tsubakimoto et al. |
| 4,771,105 A | 9/1988 | Shirai et al. |
| 4,892,598 A | 1/1990 | Stevens et al. |

(Continued)

FOREIGN PATENT DOCUMENTS

EP     1 358 894 A1     11/2003

(Continued)

OTHER PUBLICATIONS

Briggs, M., "Borates—Boron Oxides, Boric Acid, and Borates," Kirk Othmer Encyclopedia of Chemical Technology, vol. 4, 2001, pp. 259-283.

(Continued)

*Primary Examiner* — Jacqueline F Stephens
(74) *Attorney, Agent, or Firm* — Denise L. Stoker

(57) ABSTRACT

An absorbent article can have a topsheet, a backsheet, and an absorbent core disposed between the topsheet and the backsheet. In some aspects, at least one of the topsheet, backsheet, and absorbent core is stretchable. In other aspects, the absorbent core can comprise layers, at least one of which includes substantially the superabsorbent material only and at least one of which includes substantially fluff only. In some aspects, the article includes superabsorbent material having a surface additive that includes a surface crosslinking agent, a water-insoluble inorganic metal compound and a polymeric coating.

47 Claims, 13 Drawing Sheets

U.S. PATENT DOCUMENTS

| | | | |
|---|---|---|---|
| 4,940,464 A | 7/1990 | Van Gompel et al. |
| 5,114,781 A | 5/1992 | Morman |
| 5,116,662 A | 5/1992 | Morman |
| 5,145,906 A | 9/1992 | Chambers et al. |
| 5,151,092 A | 9/1992 | Buell et al. |
| 5,217,445 A | 6/1993 | Young et al. |
| 5,350,624 A | 9/1994 | Georger et al. |
| 5,387,208 A | 2/1995 | Ashton et al. |
| 5,409,771 A | 4/1995 | Dahmen et al. |
| 5,486,166 A | 1/1996 | Bishop et al. |
| 5,490,846 A | 2/1996 | Ellis et al. |
| 5,560,878 A | 10/1996 | Dragoo et al. |
| 5,562,646 A | 10/1996 | Goldman et al. |
| 5,575,783 A | 11/1996 | Clear et al. |
| 5,662,634 A | 9/1997 | Yamamoto et al. |
| 5,669,894 A | 9/1997 | Goldman et al. |
| 5,766,389 A | 6/1998 | Brandon et al. |
| 5,820,973 A | 10/1998 | Dodge, II et al. |
| 5,833,678 A | 11/1998 | Ashton et al. |
| 5,849,405 A | 12/1998 | Wang et al. |
| 5,883,028 A | 3/1999 | Morman et al. |
| 5,883,158 A | 3/1999 | Nambu et al. |
| 5,981,070 A | 11/1999 | Ishizaki et al. |
| 5,985,432 A | 11/1999 | Wang et al. |
| 6,011,196 A | 1/2000 | Wang et al. |
| 6,086,571 A | 7/2000 | Guevara et al. |
| 6,099,950 A | 8/2000 | Wang et al. |
| 6,121,409 A | 9/2000 | Mitchell et al. |
| 6,121,509 A | 9/2000 | Ashraf et al. |
| 6,222,091 B1 | 4/2001 | Beihoffer et al. |
| 6,229,062 B1 | 5/2001 | Mandell et al. |
| 6,297,335 B1 | 10/2001 | Funk et al. |
| 6,359,049 B1 | 3/2002 | Carrico et al. |
| 6,362,389 B1 | 3/2002 | McDowall et al. |
| 6,376,072 B1 | 4/2002 | Evans et al. |
| 6,380,456 B1 | 4/2002 | Goldman |
| 6,387,495 B1 | 5/2002 | Reeves et al. |
| 6,414,214 B1 | 7/2002 | Engelhardt et al. |
| 6,552,245 B1 | 4/2003 | Roessler et al. |
| 6,562,743 B1 | 5/2003 | Cook et al. |
| 6,565,768 B1 | 5/2003 | Dentler et al. |
| 6,603,055 B2 | 8/2003 | Mitchell et al. |
| 6,623,576 B2 | 9/2003 | Mitchell et al. |
| 6,641,134 B1 | 11/2003 | Dobbertin et al. |
| 6,645,190 B1 | 11/2003 | Olson et al. |
| 6,831,122 B2 | 12/2004 | Daniel et al. |
| 7,144,957 B2 | 12/2006 | Funk et al. |
| 2002/0128618 A1 | 9/2002 | Frenz et al. |
| 2003/0113463 A1 | 6/2003 | Ko et al. |
| 2003/0125684 A1 | 7/2003 | Qin |
| 2003/0131962 A1 | 7/2003 | Lindsay et al. |
| 2003/0135939 A1 | 7/2003 | Sun et al. |
| 2003/0139291 A1 | 7/2003 | Qin |
| 2003/0139714 A1 | 7/2003 | Sun et al. |
| 2003/0219594 A1 | 11/2003 | Qin et al. |
| 2004/0039074 A1 | 2/2004 | Hahnle et al. |
| 2004/0039360 A1 | 2/2004 | Ehrnsperger et al. |
| 2004/0077796 A1 | 4/2004 | Daniel et al. |
| 2004/0180189 A1 | 9/2004 | Funk et al. |
| 2004/0214946 A1 | 10/2004 | Smith et al. |
| 2005/0013992 A1 | 1/2005 | Azad et al. |
| 2005/0027268 A1 | 2/2005 | Qin et al. |
| 2005/0096435 A1 | 5/2005 | Smith et al. |
| 2005/0239942 A1 | 10/2005 | Herfert et al. |
| 2005/0245393 A1 | 11/2005 | Herfert et al. |
| 2005/0245684 A1 | 11/2005 | Daniel et al. |
| 2006/0004336 A1 | 1/2006 | Zhang et al. |
| 2006/0025030 A1 | 2/2006 | Funk et al. |
| 2006/0173431 A1 | 8/2006 | Laumer et al. |
| 2006/0173432 A1 | 8/2006 | Laumer et al. |
| 2006/0173433 A1 | 8/2006 | Laumer et al. |
| 2007/0135785 A1 | 6/2007 | Qin et al. |
| 2008/0045916 A1 | 2/2008 | Herfert et al. |
| 2008/0114129 A1 | 5/2008 | Herfert et al. |
| 2008/0166410 A1 | 7/2008 | Funk et al. |
| 2008/0187755 A1 | 8/2008 | Herfert et al. |
| 2008/0221237 A1 | 9/2008 | Herfert et al. |

FOREIGN PATENT DOCUMENTS

| | | | |
|---|---|---|---|
| EP | 1 607 412 A1 | 12/2005 |
| EP | 1 690 556 A2 | 8/2006 |
| GB | 2 151 272 A | 7/1985 |
| JP | 09-124879 A | 5/1997 |
| JP | 2004-097255 A | 4/2004 |
| WO | WO 99/25745 A1 | 5/1999 |
| WO | WO 00/37009 A2 | 6/2000 |
| WO | WO 00/46260 A1 | 8/2000 |
| WO | WO 00/55245 A1 | 9/2000 |
| WO | WO 01/32117 A1 | 5/2001 |
| WO | WO 03/104543 A1 | 12/2003 |
| WO | WO 2004/018005 A1 | 3/2004 |
| WO | WO 2004/024816 A1 | 3/2004 |
| WO | WO 2005/056070 A1 | 6/2005 |
| WO | WO 2005/094749 A2 | 10/2005 |
| WO | WO 2005/097881 A1 | 10/2005 |
| WO | WO 2006/069732 A1 | 7/2006 |
| WO | WO 2006/082188 A1 | 8/2006 |
| WO | WO 2006/082189 A1 | 8/2006 |
| WO | WO 2006/082197 A1 | 8/2006 |
| WO | WO 2007/070776 A2 | 6/2007 |

OTHER PUBLICATIONS

Hu, Z.S. and J.X. Dong, "Study on Antiwear and Reducing Friction Additive of Nanometer Titanium Borate," *Wear*, Elsevier Science, vol. 216, No. 1, 1998, pp. 87-91.

"Aluminium Sulfate," Wikipedia, the Free Encyclopedia, Internet web page "http://en.wikipedia.org/wiki/Aluminium_sulfate", viewed and printed Nov. 13, 2007, 3 pages.

"Magnesium Sulfate," Wikipedia, the Free Encyclopedia, Internet web page "http://en.wikipedia.org/wiki/Magnesium_sulfate", viewed and printed Nov. 13, 2007, 3 pages.

American Society for Testing Materials (ASTM) Designation: D1238-70, "Standard Method for Measuring Flow Rates of Thermoplastics by Extrusion Plastometer," pp. 415-426, effective Jun. 1970.

Lawrence, K.D. et al., "An Improved Device for the Formation of Superfine, Thermoplastic Fibers," *NRL Report 5265*, U.S. Naval Research Laboratory, Washington, D.C., Feb. 11, 1959, pp. 1-7.

Neumann, A.W., and R.J. Good, "Techniques of Measuring Contact Angles," Chapter 2, *Surface and Colloid Science—Experimental Methods*, vol. 11, edited by R.J. Good and R.R. Stromberg, Plenum Press, 1979, pp. 31-91.

Wente, V.A. et al., "Manufacture of Superfine Organic Fibers," *NRL Report 4364*, U.S. Naval Research Laboratory, Washington, D.C., May 25, 1954, pp. 1-15.

ABSORBENT ARTICLES COMPRISING HIGH PERMEABILITY SUPERABSORBENT POLYMER COMPOSITIONS

BACKGROUND

Articles, such as absorbent articles, are useful for absorbing many types of fluids, including fluids secreted or eliminated by the human body. Superabsorbent polymers (SAPs) are frequently used in absorbent articles to help improve the absorbent properties of such articles. SAPs are generally polymer based and are available in many forms, such as powders, granules, microparticles, films and fibers, for example. Upon contact with fluids, such SAPs swell by absorbing the fluids into their structures. In general, SAPs can quickly absorb fluids insulted into such articles, and can retain such fluids to prevent leakage and help provide a dry feel even after fluid insult.

There is a continuing effort to improve the performance of absorbent articles, especially at high levels of fluid saturation, to thereby reduce the occurrence of leakage and to improve fit and comfort. This is particularly significant when such articles are subjected to repeated fluid insults during use. This has become an increasing challenge as recent efforts in absorbent article design have generally focused on using higher concentrations of superabsorbent material and less fluff fibers to make the absorbent structures thinner and more flexible. However, notwithstanding the increase in total absorbent capacity obtained by increasing the concentration of superabsorbent material, such absorbent articles may still nevertheless leak during use. Such leakage may in part be the result of the absorbent core component of an article having an insufficient intake rate (i.e., the rate at which a fluid insult can be taken into and entrained within the absorbent core for subsequent absorption by the superabsorbent material) due to factors such as low permeability and lack of available void volume. Therefore, there is a desire for an absorbent article which contains high levels of superabsorbent materials and which can maintain a sufficient intake rate.

In addition, there is also a need for superabsorbent polymer materials that have increased permeability characteristics while retaining other characteristics such as adequate absorption and/or retention. Permeability is a measure of the effective connectedness of a porous structure, be it a mat of fiber or a slab of foam or, in this case, crosslinked polymers and may be specified in terms of the void fraction and extent of connectedness of the superabsorbent polymer material. Gel permeability is a property of the mass of particles as a whole and is related to particle size distribution, particle shape, and the connectedness of the open pores, shear modulus and surface modification of the swollen gel. In practical terms, the permeability of the superabsorbent polymer material is a measure of how rapidly liquid flows through the mass of swollen particles. Low permeability indicates that liquid cannot flow readily through the superabsorbent polymer material, which is generally referred to as gel blocking, and that any forced flow of liquid (such as a second application of urine during use of the absorbent article) must take an alternate path (e.g., leakage). Therefore, there is a need for an absorbent article which exhibits improved permeability characteristics.

One method to increase permeabilities in extremely thin diapers with low fiber content is to increase the amount of crosslinking of the superabsorbent material. However, the absorption and retention values of the superabsorbent polymer compositions may then be reduced to undesirably low levels when the crosslinking of the superabsorbent polymer is increased. Therefore, there is a further need to provide superabsorbent polymer compositions that exhibit improved application properties including a high absorption capacity to retain fluids under no load, high absorption capacities to retain fluid under pressure, and/or improved gel bed permeability.

SUMMARY

In response to the needs discussed above, an article of the present invention comprises an absorbent article which can have a topsheet, a backsheet, and an absorbent core disposed between the topsheet and the backsheet.

In some aspects, the absorbent core includes an superabsorbent polymer composition comprising a superabsorbent polymer and a surface additive, where the superabsorbent polymer comprises:

a) from about 55% to about 99.9% by weight of a polymerizable unsaturated acid-group-containing-monomer based on the superabsorbent polymer; and b) from about 0.001% to about 5% by weight of internal crosslinking agent based on the polymerizable unsaturated acid-group-containing-monomer;

where the superabsorbent polymer has a degree of neutralization of greater than about 25%; where elements a) and b) have been polymerized and prepared into superabsorbent polymer particles; and where the surface additive comprises:

i) from about 0.001% to about 5% by weight of surface crosslinking agent based on the superabsorbent polymer composition;

ii) from about 0.01% to about 2% by weight of a water-insoluble inorganic metal compound based on the superabsorbent polymer composition; and iii) from 0% to about 5% by weight of a polymeric coating based on the superabsorbent polymer composition.

In some aspects, the absorbent article at least one of the topsheet, backsheet, and absorbent core is stretchable. In other aspects, the absorbent core comprises at least about 30% by weight of the superabsorbent polymer composition, such as about 60% to about 95% by weight of the superabsorbent polymer composition. In still other aspects, the absorbent core further comprises fluff. In yet other aspects, the absorbent core further comprises a surfactant.

In some aspects, the absorbent core comprises layers. In some particular aspects, at least one of the layers comprises substantially only the superabsorbent polymer composition and at least one of the layers comprises substantially only fluff.

In some aspects, the absorbent article is selected from personal care absorbent articles, health/medical absorbent articles, household/industrial absorbent articles or sports/construction absorbent articles.

In some aspects, the superabsorbent polymer composition has been heat-treated. In some particular aspects, the superabsorbent polymer composition has been heat-treated from about 150° C. to about 250° C.

In some aspects, the superabsorbent polymer composition exhibits a centrifuge retention capacity of at least about 30 g/g as measured by the Centrifuge Retention Capacity Test and a free swell gel bed permeability of at least about 10 Darcy as measured by the Free Swell Gel Bed Permeability Test. In other aspects, the superabsorbent polymer composition exhibits a centrifuge retention capacity of at least about 32 g/g as measured by the Centrifuge Retention Capacity Test, and a free swell gel bed permeability of at least about 20 Darcy as measured by the Free Swell Gel Bed Permeability Test. In still other aspects, the superabsorbent polymer composition exhibits a centrifuge retention capacity from about 32 g/g to about 40 g/g as measured by the Centrifuge Retention Capacity Test, and a free swell gel bed permeability of at least about 40 Darcy as measured by the Free Swell Gel Bed Permeability Test.

In some aspects, the water-insoluble inorganic metal compound is selected from a metal phosphate, titanium borate, aluminum borate, iron borate, magnesium borate, manganese borate, and calcium borate. In other aspects, the metal phosphate is aluminum phosphate. In still other aspects, particles of the inorganic metal compound have a mass median particle size of less than about 2 μm.

In some aspects, the polymeric coating is from about 0.01% to about 0.5% by weight of a thermoplastic polymer based on the superabsorbent polymer composition. In other aspects, the polymeric coating is selected from polyolefin, polyethylene, polyesters, polyurethanes, linear low density polyethylene, ethylene acrylic acid copolymer, styrene copolymers, ethylene alkyl methacrylate copolymer, polypropylene, maleated polypropylene, ethylene vinyl acetate copolymer, polyamide, polyester, or blends and copolymers thereof. In still other aspects, the polymeric coating is a cationic polymer. In yet other aspects, the polymeric coating is a polyvinylamine. In still other aspects, the polymeric coating is a blend of maleated polypropylene and ethylene acrylic acid copolymer.

In some aspects, at least about 40% by weight of the superabsorbent polymer composition has a particle size from about 300 μm to about 600 μm. In other aspects, at least about 50% by weight of the superabsorbent polymer composition has a particle size from about 300 μm to about 600 μm.

In some aspects, at least about 50 wt % of acid groups of the polymerizable unsaturated acid-group-containing-monomer include carboxyl groups; where the acid groups have been neutralized to at least 50 mol %; and where the internal crosslinking agent is from about 0.2 wt % to about 3 wt % based on the total amount of the polymerizable unsaturated acid-group-containing-monomer.

In some aspects, the water-insoluble inorganic metal compound has been applied to the surface of the superabsorbent polymer particles in suspension form. In other aspects, the water-insoluble, inorganic metal compound has been applied to the surface of the superabsorbent polymer particles in dry form.

In one aspect, an absorbent article comprises an absorbent core, where the absorbent core includes a superabsorbent polymer composition comprising superabsorbent polymer particles that have been surface treated with from about 0.01 to about 2% by weight of an inorganic metal compound selected from insoluble aluminum phosphate or an insoluble metal borate, based on the superabsorbent polymer composition.

In some aspects, the absorbent article further comprises a topsheet and a backsheet, where the absorbent core is disposed between the topsheet and the backsheet. In other aspects, at least one of the topsheet, backsheet, and absorbent core is stretchable.

In some aspects, the absorbent core comprises at least about 30% by weight of the superabsorbent polymer composition. In some particular aspects, the absorbent core comprises about 60% to about 95% by weight of the superabsorbent polymer composition.

In some aspects, the absorbent core further comprises fluff. In other aspects, the absorbent core further comprises a surfactant.

In some aspects, the absorbent core comprises layers. In some particular aspects, at least one of the layers comprises substantially the superabsorbent polymer composition and at least one of the layers comprises substantially fluff.

In some aspects, the article is selected from personal care absorbent articles, health/medical absorbent articles, household/industrial absorbent articles or sports/construction absorbent articles.

In some aspects, the superabsorbent polymer composition exhibits a free swell gel bed permeability of at least about 10 Darcy as measured by the Free Swell Gel Bed Permeability Test. In other aspects, the superabsorbent polymer composition exhibits a centrifuge retention capacity of at least about 32 g/g as measured by the Centrifuge Retention Capacity Test, and a free swell gel bed permeability of at least about 20 Darcy as measured by the Free Swell Gel Bed Permeability Test.

In some aspects, the insoluble metal borate is selected from titanium borate, aluminum borate, iron borate magnesium borate, manganese borate, and calcium borate. In other aspects, particles of the inorganic metal compound have a median particle size of less than about 2 μm.

In some aspects, at least about 40% by weight of the superabsorbent polymer composition has a particle size from about 300 μm to about 600 μm.

In one aspect, an absorbent article comprises an absorbent core; where the absorbent core includes a superabsorbent polymer composition that has been prepared by: a) providing superabsorbent polymer particles; b) preparing a first solution of a first inorganic metal salt; c) preparing a second solution of a second inorganic metal salt; and d) applying the first solution and second solution to the superabsorbent polymer particles to form a water-insoluble inorganic metal salt precipitate directly on or in the vicinity of a surface of the superabsorbent polymer particles.

In some aspects, the absorbent article further comprises a topsheet and a backsheet, wherein the absorbent core is disposed between the topsheet and the backsheet.

In some aspects, the first inorganic metal salt includes a cation selected from aluminum, titanium, calcium or iron and the second inorganic metal salt includes an anion selected from phosphate, borate or chromate. In other aspects, the first inorganic metal salt is aluminum sulfate tetradecahydrate trisodium phosphate and the second inorganic metal salt is trisodium phosphate.

Numerous other features and advantages of the present invention will appear from the following description. In the description, reference is made to exemplary embodiments of the invention. Such embodiments do not represent the full scope of the invention. Reference should therefore be made to the claims herein for interpreting the full scope of the invention. In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

FIGURES

The foregoing and other features, aspects and advantages of the present invention will become better understood with regard to the following description, appended claims and accompanying drawings where:

Figure 1:
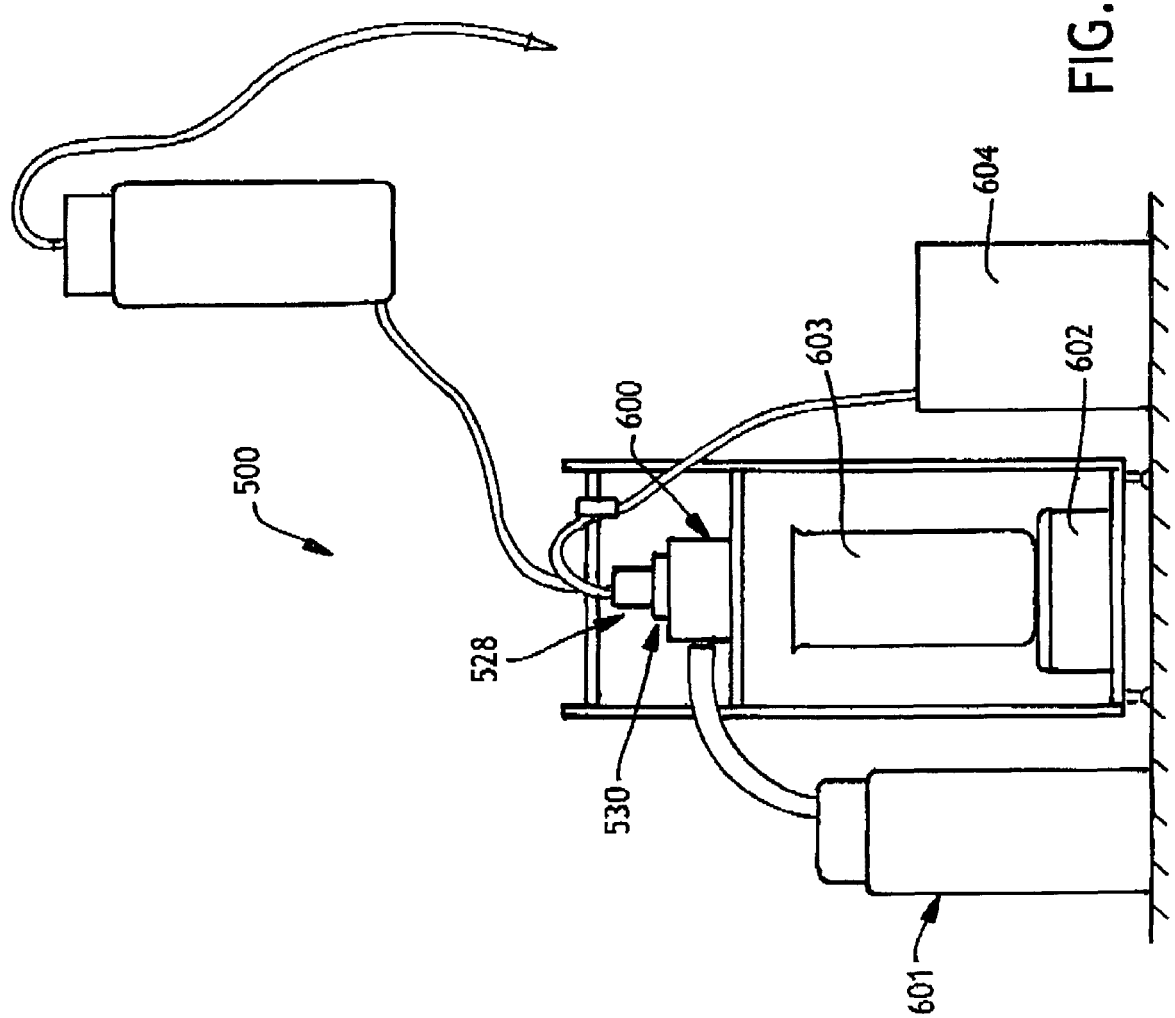
FIG. 1 is a side view of the test apparatus employed for the Free Swell Gel Bed Permeability Test.

Repeated use of reference characters in the present specification and drawings is intended to represent the same or analogous features or elements of the present invention.

Test Methods
Centrifuge Retention Capacity Test (CRC)

This test determines the free swelling capacity of a hydrogel-forming polymer. The resultant retention capacity is stated as grams of liquid retained per gram weight of the sample (g/g). In this method, 0.2000±0.0050 g of dry superabsorbent polymer composition particles of size fraction 300 to 600 μm are inserted into a teabag. The superabsorbent polymer composition particles can be pre-screened with, for example, a RO-TAP Mechanical Sieve Shaker Model B available from W. S. Tyler, Inc., Mentor, Ohio. Sieving is conducted for 10 minutes. A heat-sealable tea bag material, such as that available from Dexter Corporation (having a place of business in Windsor Locks, Conn., U.S.A.) as model designation 1234T heat sealable filter paper works well for most applications. The bag is formed by folding a 5-inch by 3-inch (12.7-cm×7.6-cm) sample of the bag material in half and heat-sealing two of the open edges to form a 2.5-inch by 3-inch (6.4-cm×7.6-cm) rectangular pouch. The heat seals are about 0.25 inches inside the edge of the material. After the sample is placed in the pouch, the remaining open edge of the pouch is also heat-sealed. Empty bags can also be made to serve as controls. The teabag is placed in saline solution (i.e., 0.9 wt % aqueous sodium chloride) for 30 minutes (at least 0.83 l (liter) saline solution/1 g polymer), making sure that the bags are held down until they are completely wetted. Then, the teabag is centrifuged for 3 minutes at 290 g force with a variance from about 286 to about 292 g force). G force is defined as a unit of inertial force on a body that is subjected to rapid acceleration or gravity, equal to 32 ft/sec/sec at sea level. The absorbed quantity of saline solution is determined by measuring the weight of the teabag. The amount of solution retained by the superabsorbent polymer composition sample, taking into account the solution retained by the bag itself, is the Centrifuge Retention Capacity (CRC) of the superabsorbent polymer composition, expressed as grams of fluid per gram of superabsorbent polymer composition. More particularly, the retention capacity is determined by the following equation:

$$\frac{[\text{sample/bag wt. after centrifuge}] - [\text{empty bag wt. after centrifuge}] - [\text{dry sample wt.}]}{[\text{dry sample wt.}]}$$

Water Content

The amount of water content, measured as "% moisture," can be measured as follows: 1) Weigh 4.5-5.5 grams of superabsorbent polymer composition (SAP) accurately in a pre-weighed aluminum weighing pan; 2) place the SAP and pan into a standard lab oven preheated to 150° C. for 30 minutes; 3) remove and re-weigh the pan and contents; and 4) calculate the percent moisture using the following formula:

$$\% \text{ Moisture} = \{((\text{pan wt} + \text{initial SAP wt}) - (\text{dried SAP \& pan wt}))*100\}/\text{dried SAP wt}$$

Free-Swell Gel Bed Permeability Test (FSGBP)

Figure 2:
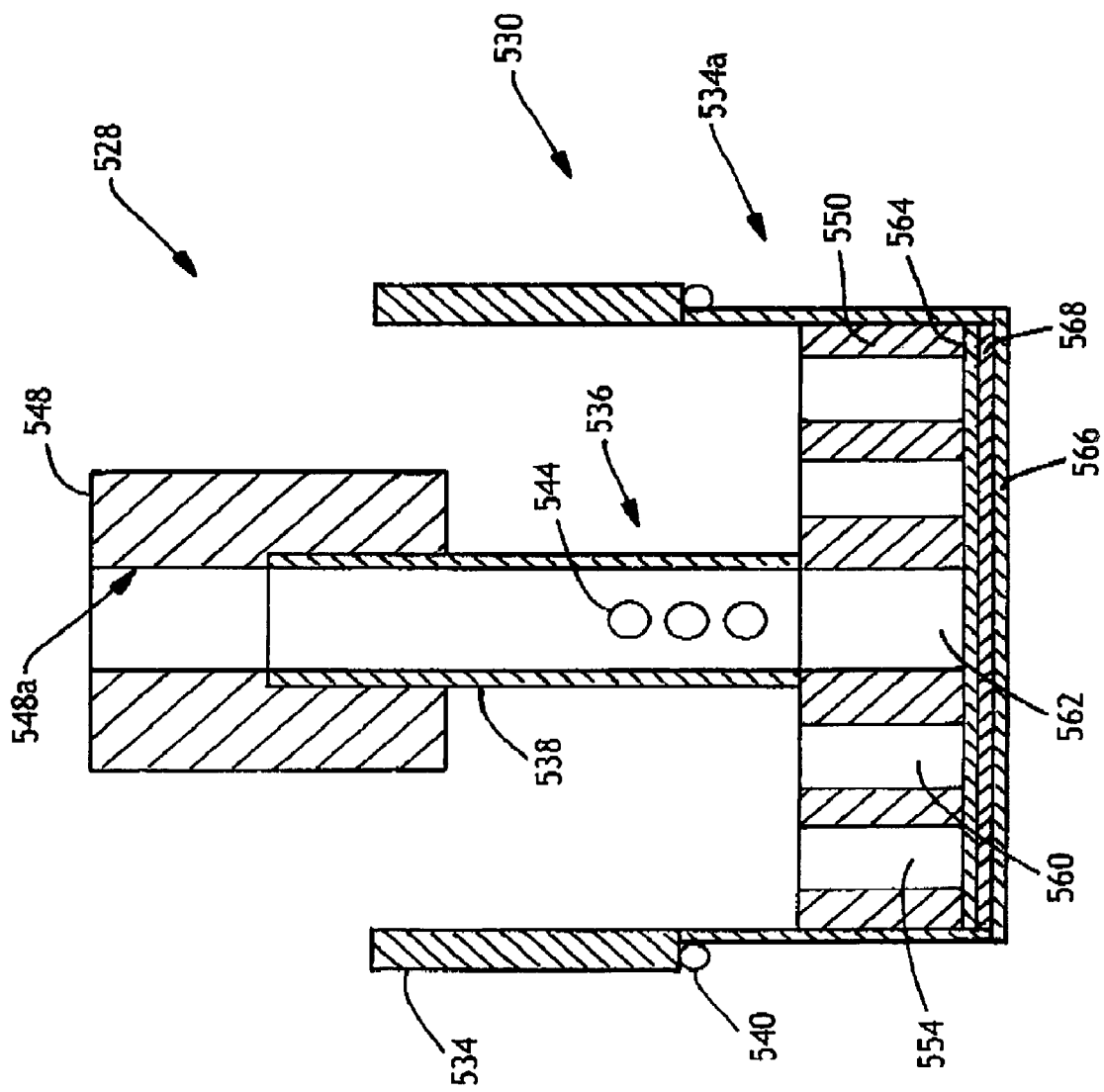
FIG. 2 is a cross-sectional side view of a cylinder/cup assembly employed in the Free Swell Gel Bed Permeability Test apparatus shown in FIG. 1.
Figure 3:
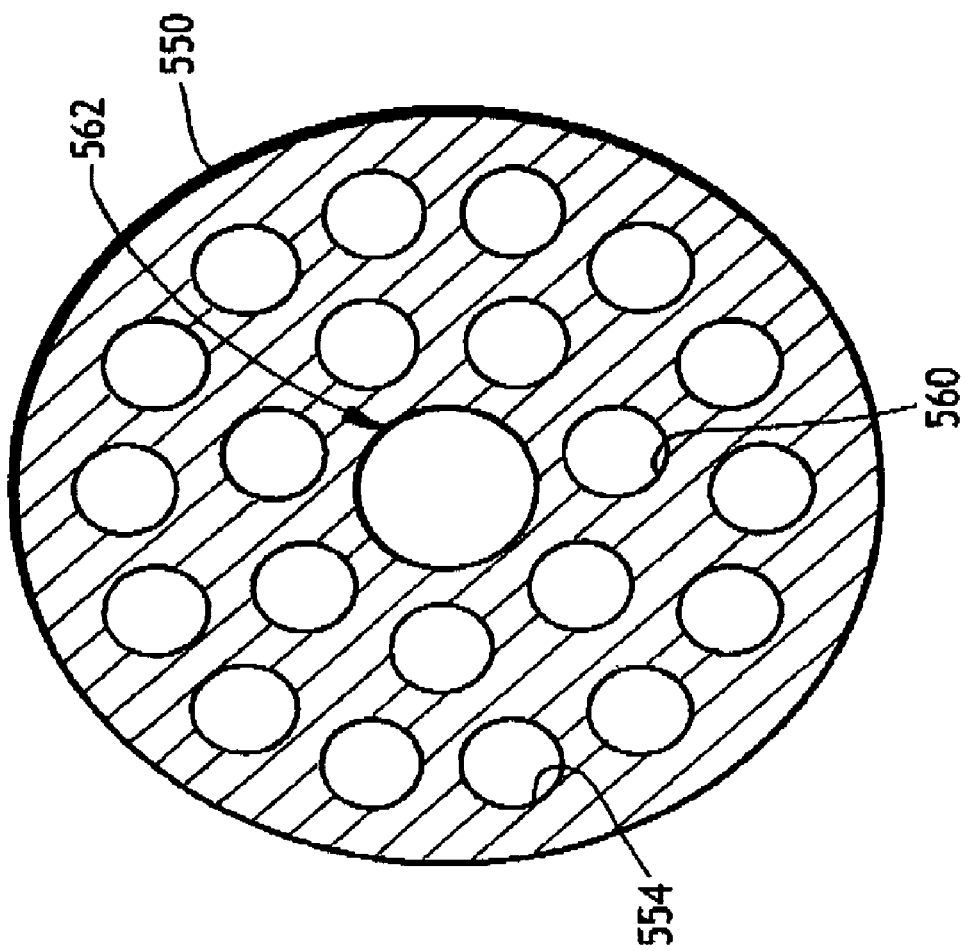
FIG. 3 is a top view of a plunger employed in the Free Swell Gel Bed Permeability Test apparatus shown in FIG. 1.

As used herein, the Free-Swell Gel Bed Permeability Test, also referred to as the Gel Bed Permeability (GBP) Under 0 psi Swell Pressure Test, determines the permeability of a swollen bed of gel particles (e.g., such as the surface treated absorbent material or the superabsorbent material prior to being surface treated), under what is commonly referred to as "free swell" conditions. The term "free swell" means that the superabsorbent polymer composition particles are allowed to swell without a restraining load upon absorbing test solution as will be described. A suitable apparatus for conducting the Gel Bed Permeability Test is shown in FIGS. 1, 2 and 3 and indicated generally at 500. The test apparatus assembly 528 comprises a sample container, generally indicated at 530, and a plunger, generally indicated at 536. The plunger comprises a shaft 538 having a cylinder hole bored down the longitudinal axis and a plunger head 550 positioned at the bottom of the shaft. The shaft hole 562 has a diameter of about 16 mm. The plunger head is attached to the shaft, such as by adhesion. Twelve holes 544 are bored into the radial axis of the shaft, three positioned at every 90 degrees having diameters of about 6.4 mm. The shaft 538 is machined from a LEXAN rod or equivalent material and has an outer diameter of about 2.2 cm and an inner diameter of about 16 mm.

The plunger head 550 has a concentric inner ring of seven holes 560 and an outer ring of 14 holes 554, all holes having a diameter of about 8.8 millimeters as well as a hole of about 16 mm aligned with the shaft. The plunger head 550 is machined from a LEXAN rod or equivalent material and has a height of approximately 16 mm and a diameter sized such that it fits within the cylinder 534 with minimum wall clearance but still slides freely. The total length of the plunger head 550 and shaft 538 is about 8.25 cm, but can be machined at the top of the shaft to obtain the desired mass of the plunger 536. The plunger 536 comprises a 100 mesh stainless steel cloth screen 564 that is biaxially stretched to tautness and attached to the lower end of the plunger 536. The screen is attached to the plunger head 550 using an appropriate solvent that causes the screen to be securely adhered to the plunger head 550.

Care must be taken to avoid excess solvent migrating into the open portions of the screen and reducing the open area for liquid flow. Acrylic solvent Weld-On 4 from IPS Corporation (having a place of business in Gardena, Calif., U.S.A.) is a suitable solvent.

The sample container 530 comprises a cylinder 534 and a 400 mesh stainless steel cloth screen 566 that is biaxially stretched to tautness and attached to the lower end of the cylinder 534. The screen is attached to the cylinder using an appropriate solvent that causes the screen to be securely adhered to the cylinder. Care must be taken to avoid excess solvent migrating into the open portions of the screen and reducing the open area for liquid flow. Acrylic solvent Weld-On 4 from IPS Corporation (having a place of business in Gardena, Calif., U.S.A.) is a suitable solvent. A gel particle sample, indicated as 568 in FIG. 2, is supported on the screen 566 within the cylinder 534 during testing.

The cylinder 534 may be bored from a transparent LEXAN rod or equivalent material, or it may be cut from a LEXAN tubing or equivalent material, and has an inner diameter of about 6 cm (e.g., a cross-sectional area of about 28.27 cm$^2$), a wall thickness of about 0.5 cm and a height of approximately 7.95 cm. A step is machined into the outer diameter of the cylinder 534 such that a region 534a with an outer diameter of 66 mm exists for the bottom 31 mm of the cylinder 534. An o-ring 540 which fits the diameter of region 534a may be placed at the top of the step.

The annular weight 548 has a counter-bored hole about 2.2 cm in diameter and 1.3 cm deep so that it slips freely onto the shaft 538. The annular weight also has a thru-bore 548a of about 16 mm. The annular weight 548 can be made from stainless steel or from other suitable materials resistant to corrosion in the presence of the test solution, which is 0.9 weight percent sodium chloride solution in distilled water. The combined weight of the plunger 536 and annular weight 548 equals approximately 596 grams (g), which corresponds to a pressure applied to the sample 568 of about 0.3 pounds per square inch (psi), or about 20,700 dynes/cm$^2$ (2.07 kPa), over a sample area of about 28.27 cm$^2$.

When the test solution flows through the test apparatus during testing as described below, the sample container 530 generally rests on a weir 600, as seen in FIG. 1. The purpose of the weir is to divert liquid that overflows the top of the sample container 530 and diverts the overflow liquid to a separate collection device 601. The weir can be positioned above a scale 602 with a beaker 603 resting on it to collect saline solution passing through the swollen sample 568 (FIG. 2).

To conduct the Gel Bed Permeability Test under "free swell" conditions, the plunger 536, with the weight 548 seated thereon, is placed in an empty sample container 530 and the height from the top of the weight 548 to the bottom of the sample container 530 is measured using a suitable gauge accurate to 0.01 mm. The force the thickness gauge applies during measurement should be as low as possible, preferably less than 75 grams. It is important to measure the height of each empty sample container 530, plunger 536, and weight 458 combination and to keep track of which plunger 536 and weight 548 is used when using multiple test apparatus. The same plunger 536 and weight 548 should be used for measurement when the sample 568 is later swollen following saturation. It is also important that the base that the sample cup 530 is resting on is level, and the top surface of the weight 548 is parallel to the bottom surface of the sample cup 530.

The sample to be tested is prepared from superabsorbent polymer composition particles which are prescreened through a U.S. standard 30 mesh screen and retained on a U.S. standard 50 mesh screen. As a result, the test sample comprises particles sized in the range of about 300 to about 600 microns. The particles can be prescreened by hand or automatically. The superabsorbent polymer particles can be pre-screened with, for example, a RO-TAP Mechanical Sieve Shaker Model B available from W. S. Tyler, Inc., Mentor, Ohio. Sieving is conducted for 10 minutes. Approximately 2.0 grams of the sample is placed in the sample container 530 and spread out evenly on the bottom of the sample container. The container, with 2.0 grams of sample in it, without the plunger 536 and weight 548 therein, is then placed in a reservoir (not shown) containing saline solution (i.e., 0.9 wt % aqueous sodium chloride) for a time period of about 60 minutes to saturate the sample and allow the sample to swell free of any restraining load. During saturation, the sample cup 530 is set on a mesh (not shown) located in the liquid reservoir so that the sample cup 530 is raised slightly above the bottom of the liquid reservoir. The mesh does not inhibit the flow of saline solution into the sample cup 530. A suitable mesh can be obtained as part number 7308 from Eagle Supply and Plastic, having a place of business in Appleton, Wis., U.S.A. Saline does not fully cover the superabsorbent, as would be evidenced by a perfectly flat saline surface in the test cell. Saline depth is not allowed to fall so low that the surface within the cell is defined solely by swollen superabsorbent.

At the end of this period, the plunger 536 and weight 548 assembly is placed on the saturated sample 568 in the sample container 530 and then the sample container 530, plunger 536, weight 548, and sample 568 are removed from the solution. The thickness of the saturated sample 568 is determined by again measuring the height from the top of the weight 548 to the bottom of the sample container 530, using the same thickness gauge used previously provided that the zero point is unchanged from the initial height measurement. During the thickness measurements, the sample container 530, plunger 536, weight 548, and sample 568 combination is placed on a flat, large grid non-deformable plate of uniform thickness that will prevent liquid in the sample container from being released onto a flat surface due to surface tension. The plate has an overall dimension of 7.6 cm by 7.6 cm, and each grid has a cell size dimension of 1.59 cm long by 1.59 cm wide by 1.12 cm deep. A suitable flat, large grid non-deformable plate material is a parabolic diffuser panel, catalogue number 1624K27, available from McMaster Carr Supply Company (having a place of business in Chicago, Ill., U.S.A.) which can then be cut to the desired dimensions. This flat, large mesh non-deformable plate must also be present when measuring the height of the initial empty assembly. The height measurement should be made as soon as practicable after the thickness gauge is engaged. The height measurement obtained from measuring the empty sample container 530, plunger 536, and weight 548 is subtracted from the height measurement obtained after saturating the sample 568. The resulting value is the thickness, or height "H" of the swollen sample.

The permeability measurement is initiated by delivering a flow of the 0.9% saline solution into the sample container 530 with the saturated sample 568, plunger 536, and weight 548 inside. The flow rate of test solution into the container is adjusted to cause saline solution to overflow the top of the cylinder 534 thereby resulting in a consistent head pressure equal to the height of the sample container 530. The test solution may be added by any suitable means that is sufficient to ensure a small, but consistent amount of overflow from the top of the cylinder, such as with a metering pump 604. The overflow liquid is diverted into a separate collection device 601. The quantity of solution passing through the sample 568 versus time is measured gravimetrically using the scale 602 and beaker 603. Data points from the scale 602 are collected every second for at least sixty seconds once the overflow has begun. Data collection may be done manually or with data collection software. The flow rate, Q, through the swollen sample 568 is determined in units of grams/second (g/s) by a linear least-square fit of the data points of the fluid passing through the sample 568 (in grams) versus time (in seconds).

Permeability in $cm^2$ is obtained by the following equation: $K=[Q*H*\mu]/[A*\rho*P]$, where K=Permeability ($cm^2$), Q=flow rate (g/sec), H=height of swollen sample (cm), $\mu$=liquid viscosity (poise) (approximately one centipoise for the test solution used with this Test), A=cross-sectional area for liquid flow (28.27 $cm^2$ for the sample container used with this Test), $\rho$=liquid density ($g/cm^3$) (approximately one $g/cm^3$, for the test solution used with this Test) and P=hydrostatic pressure ($dynes/cm^2$) (normally approximately 7,797 $dynes/cm^2$). The hydrostatic pressure is calculated from $P=\rho*g*h$, where $\rho$=liquid density ($g/cm^3$), g=gravitational acceleration, nominally 981 $cm/sec^2$, and h=fluid height, e.g., 7.95 cm for the Gel Bed Permeability Test described herein.

A minimum of two samples is tested and the results are averaged to determine the gel bed permeability of the sample.

Absorbency Under Load Test (AUL)

The Absorbency Under Load (AUL) Test measures the ability of the superabsorbent polymer particles to absorb saline solution at room temperature (test solution) while the material is under a 0.9 psi load. The apparatus for testing AUL consists of:

An AUL assembly including a cylinder, a 4.4 g piston, and a 317 gram weight. The components of this assembly are described in additional detail below.

A flat-bottomed plastic tray that is sufficiently broad to allow the glass frits to lay on the bottom without contact with the tray walls. A plastic tray that is 9 inches by 9 inches (22.9 cm×22.9 cm), with a depth of 0.5 to 1 inch (1.3 to 2.5 cm) is commonly used for this test method.

A 12.5 cm diameter sintered glass frit with a 'C' porosity (25-50 microns). This frit is prepared in advance through equilibration in saline. In addition to being washed with at least two portions of fresh saline, the frit must be immersed in saline for at least 12 hours prior to AUL measurements.

Whatman Grade 1, 12.5 cm diameter filter paper circles.

A supply of saline (0.9% sodium chloride in distilled water, by weight).

Figure 4:
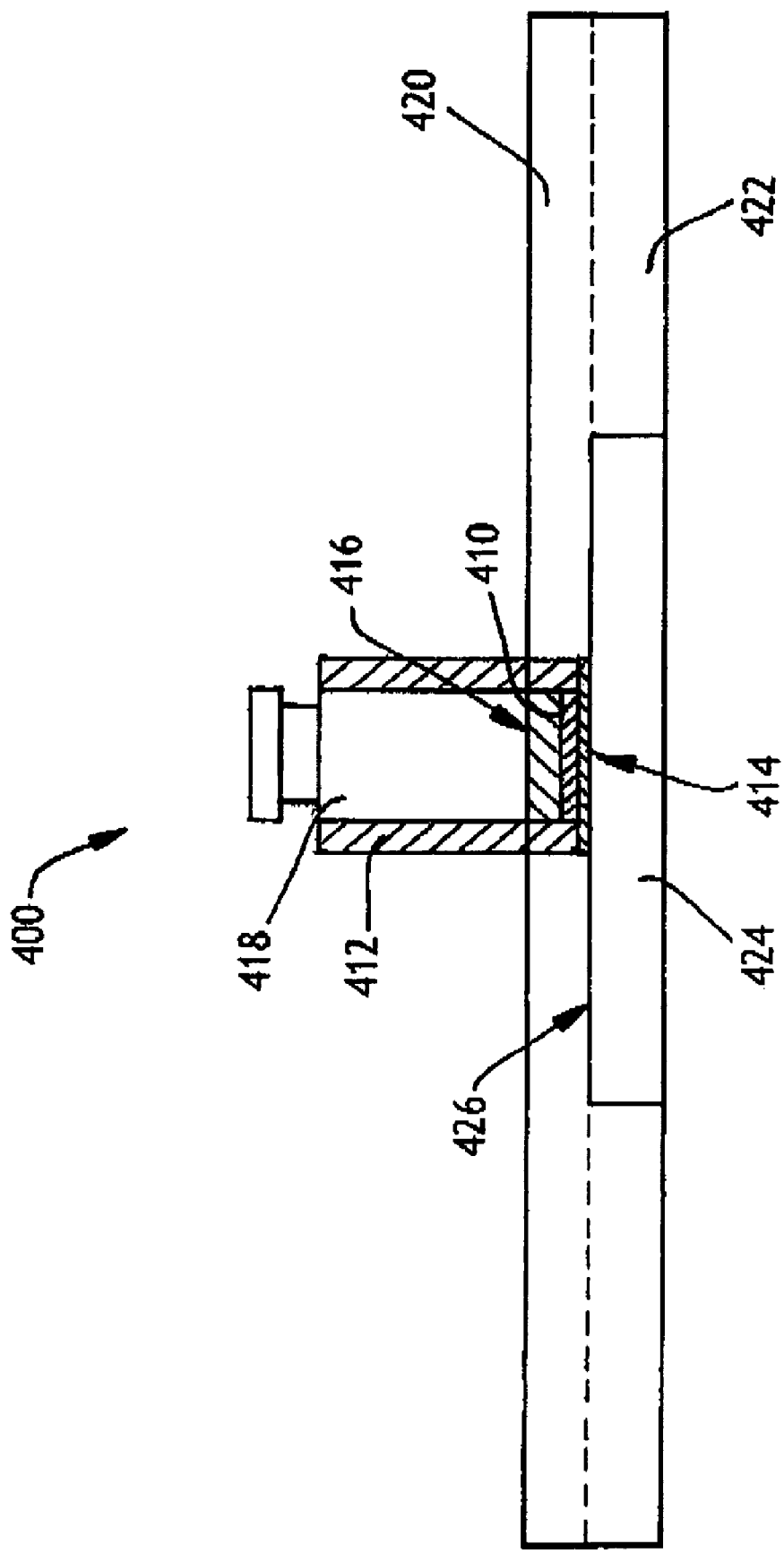
FIG. 4 is a side view of the test apparatus employed for the Absorbency Under Load Test.

Referring to FIG. 4, the cylinder 412 of the AUL assembly 400 used to contain the superabsorbent polymer composition 410 is made from one-inch (2.54 cm) inside diameter clear acrylic tubing machined-out slightly to be sure of concentricity. After machining, a 400 mesh stainless steel wire cloth 414 is attached to the bottom of the cylinder 412 using an appropriate solvent that causes the screen to be securely adhered to the cylinder. Care must be taken to avoid excess solvent migrating into the open portions of the screen and reducing the open area for liquid flow. Acrylic solvent Weld-On 4 from IPS Corporation (having a place of business in Gardena, Calif., U.S.A.) is a suitable solvent. A soldering iron can be utilized to touch up the seal if unsuccessful or if it breaks. Care must be taken to maintain a flat smooth bottom and not distort the inside of the cylinder 412.

The 4.4 g piston 416 is made from 1-inch (2.5 cm) diameter solid material (e.g., PLEXIGLAS) and is machined to closely fit without binding in the cylinder 412.

A 317 gram weight 418 is used to provide a 62,053 dyne/$cm^2$ (about 0.9 psi) restraining load. The weight is a cylindrical, 1 inch (2.5 cm) diameter, stainless steel weight that is machined to closely fit without binding in the cylinder.

Unless specified otherwise, a sample 410 corresponding to a layer of at least about 300 gsm (0.16 g) of superabsorbent polymer particles is utilized for testing the AUL. The sample 410 is taken from superabsorbent polymer composition particles that are pre-screened through U.S. standard #30 mesh and retained on U.S. std. #50 mesh. The superabsorbent polymer composition particles can be pre-screened with, for example, a RO-TAP Mechanical Sieve Shaker Model B available from W. S. Tyler, Inc., Mentor, Ohio. Sieving is conducted for 10 minutes.

The desired amount of the sample of sieved superabsorbent polymer composition particles 410 (about 0.16 g) is weighed out on a weigh paper and evenly distributed on the wire cloth 414 at the bottom of the cylinder 412. The weight of the superabsorbent polymer composition in the bottom of the cylinder is recorded as 'SA,' for use in the AUL calculation described below. Care is taken to be sure no superabsorbent polymer composition particles cling to the wall of the cylinder. The inside of the cylinder 412 is wiped with an antistatic cloth prior to placing the superabsorbent polymer composition particles 410 into the cylinder 412. After carefully placing the 4.4 g piston 412 and 317g weight 418 on the superabsorbent polymer composition particles 410 in the cylinder 412, the AUL assembly 400 including the cylinder, piston, weight, and superabsorbent polymer composition is weighed, and the weight is recorded as weight 'A'.

The sintered glass frit 424 (described above) is placed in the plastic tray 420, with saline 422 added to a level equal to that of the upper surface of the glass flit 424. A single circle of filter paper 426 is placed gently on the glass frit, and the AUL assembly 400 with the superabsorbent polymer particles 410 is then placed on top of the filter paper 426. The AUL assembly 400 is then allowed to remain on top of the filter paper 426 for a test period of one hour, with attention paid to keeping the saline level in the tray constant. At the end of the one hour test period, the AUL apparatus is then weighed, with this value recorded as weight 'B.'

The AUL(0.9 psi) is calculated as follows:

$$AUL(0.9\ psi)=(B-A)/SA$$

wherein:

A=Weight of AUL Unit with dry SAP;

B=Weight of AUL Unit with SAP after 60 minutes absorption; and

SA=Actual SAP weight.

A minimum of two tests are performed and the results are averaged to determine the AUL value under 0.9 psi load. The samples are tested at about 23° C. and about 50% relative humidity.

Saturated Capacity Test

Figure 5:
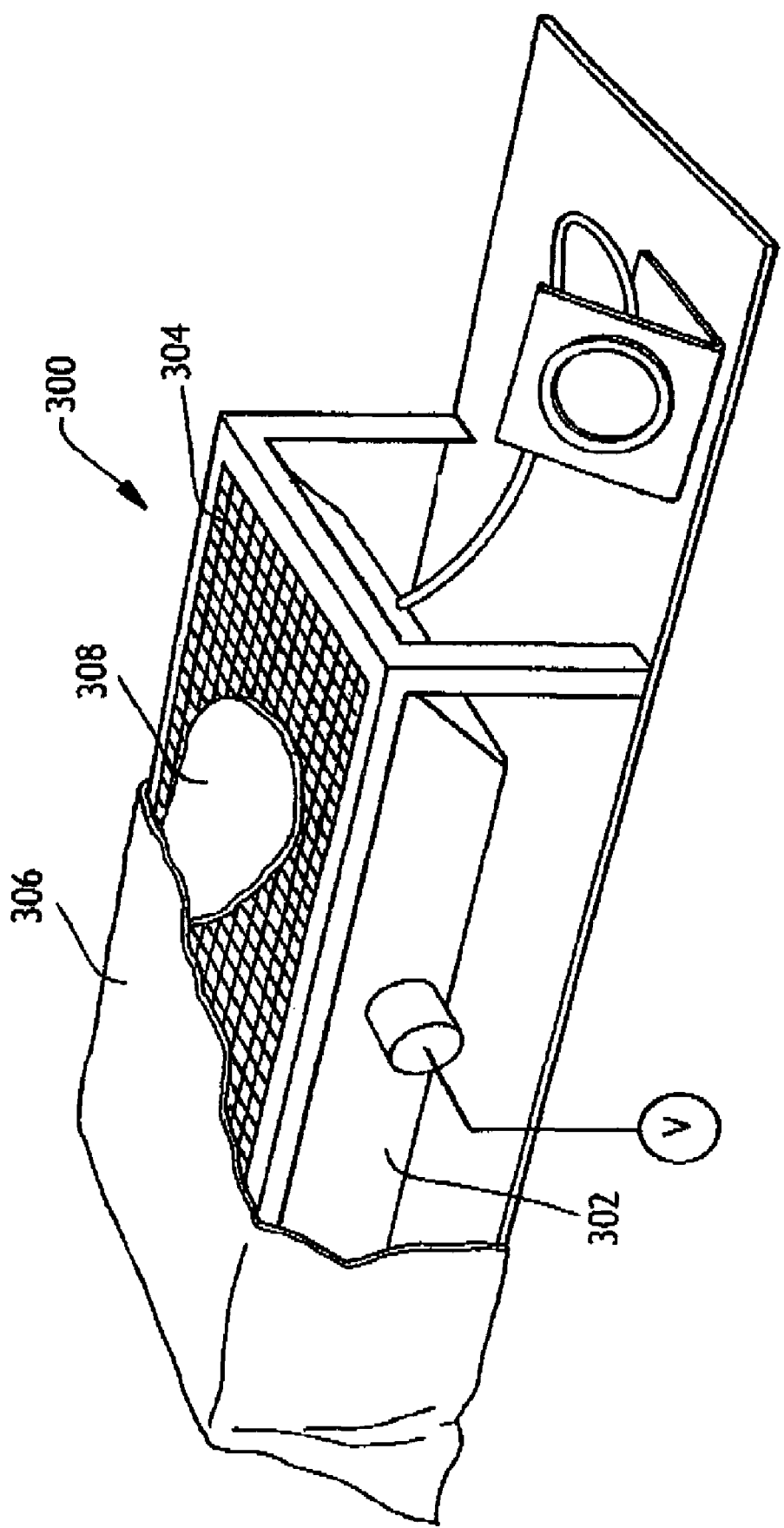
FIG. 5 is a partially cut away top view of a Saturated Capacity tester.

The following test is used to determine the saturation capacity of an absorbent composite. With reference to FIG. 5, a circular absorbent structure sample having a diameter of approximately 3 inches (7.6 cm) is weighed and the weight in grams is recorded. The sample 308 is then submerged in an excess quantity of saline solution (i.e., 0.9 wt % aqueous sodium chloride) at room temperature (e.g., about 23 degrees Celsius) for about 20 minutes. After this time period, the sample 308 is removed from the test solution and placed on a test apparatus, indicated generally at 300 in FIG. 5, comprising a vacuum box 302, a TEFLON coated fiberglass screen 304 having 0.25 inch (0.6 cm) openings (Part # 8308, available from Eagle Supply & Plastic, having a place of business in Appleton, Wis., U.S.A.) and supported from underneath by a fluorescent light diffuser panel (not shown) and horizontal rods (not shown) to prevent the fiberglass screen 304 from being deformed during the application of the vacuum. A suitable diffuser panel can be obtained as part number 1624K46 from McMaster-Carr Supply Co. (having a place of business in Chicago, Ill., U.S.A.). The diffuser panel can suitably be supported from underneath with three horizontal acrylic rods of ¾" diameter equally spaced across the width of the vacuum box. The apparatus 300 also includes a surgical grade latex cover 306 (Part # 8611K16, available from McMaster Carr Supply Company, having a place of business in Chicago, Ill., U.S.A.) sized for overlaying the screen on the vacuum box. The latex is draped over the sample and the entire opening of the vacuum box to form a seal.

More particularly, the absorbent composite sample 308 is placed on the screen. The latex cover 306 is then placed over the sample 308 and screen 304 (i.e., to generally form a seal over the vacuum box 302) and a vacuum (V) of about 0.5 pounds/square inch (about 34,474 dynes/square cm) is drawn on the vacuum box (and hence the sample) for a period of 5 minutes. The sample 308 is removed from the apparatus and weighed. The weight in grams is recorded.

If the absorbent sample has low integrity or disintegrates during the soak or transfer procedures, the absorbent sample can be wrapped in a containment material such as paper toweling, for example SCOTT paper towels manufactured by Kimberly-Clark Corporation, having a place of business in Neenah, Wis., U.S.A. The absorbent sample can be tested with the overwrap in place and the capacity of the overwrap can be independently determined and subtracted from the wet weight of the total wrapped absorbent sample to obtain the wet absorbent weight.

The overall capacity of each absorbent sample is determined by subtracting the dry weight of each absorbent sample from the wet weight of that absorbent sample, determined at this point in the procedure. The Saturated Capacity of the absorbent structure is determined by the following formula:

Saturated Capacity=(wet weight−dry weight)/dry weight;

wherein the Saturated Capacity value has units of grams of fluid/gram of absorbent. For Saturated Capacity, a minimum of three specimens of each sample should be tested and the results averaged.

At least three samples of each absorbent structure are tested and the results are averaged to provide the saturation capacity of the absorbent composite.

Fluid Intake Rate Test

Figure 6:
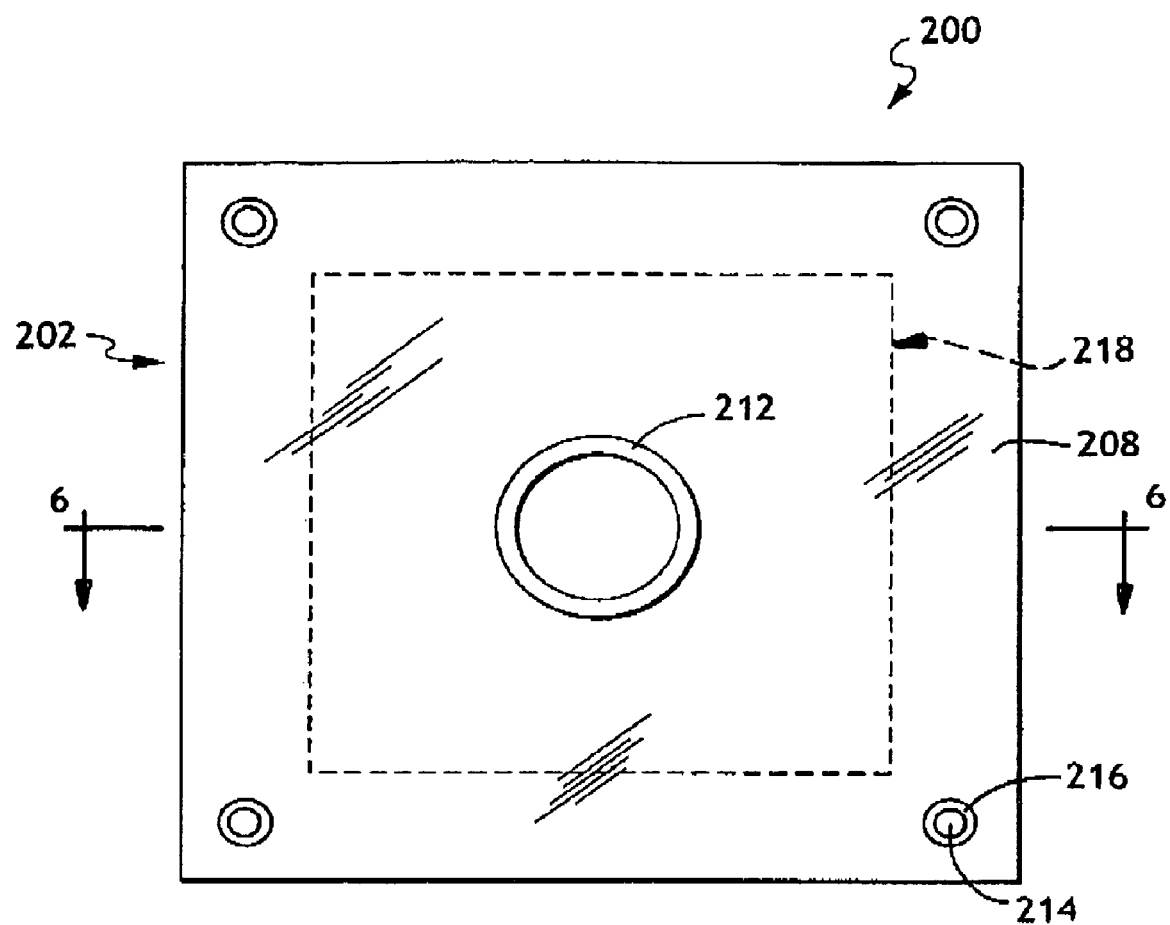
FIG. 6 is a top view of the test apparatus employed for the Fluid Intake Rate Test.
Figure 7:
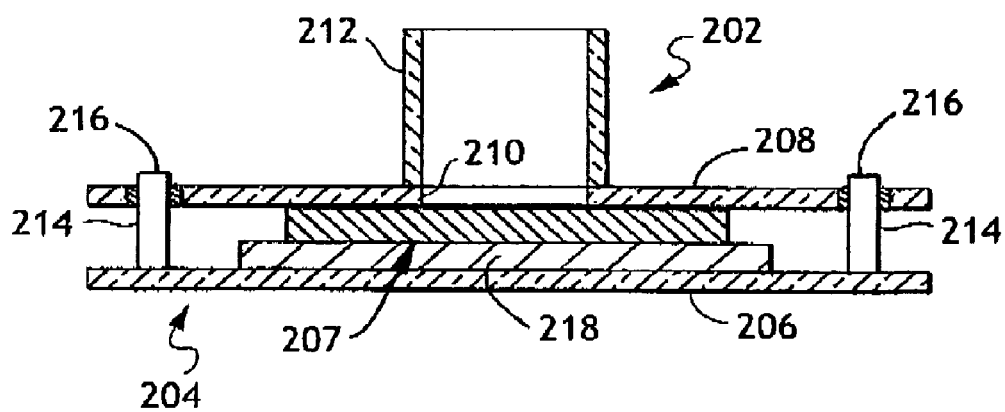
FIG. 7 is a cross-sectional side view taken along line 6-6 of the test apparatus employed for the Fluid Intake Rate Test shown in FIG. 6.

The Fluid Intake Rate (FIR) Test determines the amount of time required for an absorbent structure to take in (but not necessarily absorb) a known amount of saline test solution (0.9 weight percent solution of sodium chloride in distilled water at room temperature). A suitable apparatus for performing the FIR Test is shown in FIGS. 6 and 7 and is generally indicated at 200. The test apparatus 200 comprises upper and lower assemblies, generally indicated at 202 and 204 respectively, wherein the lower assembly comprises a generally 7 inch by 7 inch (17.8 cm×17.8 cm) square lower plate 206 constructed of a transparent material such as PLEXIGLAS (available from Degussa AG, a business having offices located in Dusseldorf, Germany) for supporting the absorbent sample during the test and a generally 4.5 inch by 4.5 inch (11.4 cm×11.4 cm) square platform 218 centered on the lower plate 206.

The upper assembly 202 comprises a generally square upper plate 208 constructed similar to the lower plate 206 and having a central opening 210 formed therein. A cylinder (fluid delivery tube) 212 having an inner diameter of about one inch (2.5 cm) is secured to the upper plate 208 at the central opening 210 and extends upward substantially perpendicular to the upper plate. The central opening 210 of the upper plate 208 should have a diameter at least equal to the inner diameter of the cylinder 212 where the cylinder 212 is mounted on top of the upper plate 208. However, the diameter of the central opening 210 may instead be sized large enough to receive the outer diameter of the cylinder 212 within the opening so that the cylinder 212 is secured to the upper plate 208 within the central opening 210.

Pin elements 214 are located near the outside corners of the lower plate 206, and corresponding recesses 216 in the upper plate 208 are sized to receive the pin elements 214 to properly align and position the upper assembly 202 on the lower assembly 204 during testing. The weight of the upper assembly 202 (e.g., the upper plate 208 and cylinder 212) is approximately 360 grams to simulate approximately 0.11 pounds/square inch(psi) pressure on the absorbent sample during the FIR Test.

To run the FIR Test, an absorbent sample 207 being 3 inches (7.6 cm) in diameter is weighed and the weight is recorded in grams. The sample 207 is then centered on the platform 218 of the lower assembly 204. The upper assembly 202 is placed over the sample 207 in opposed relationship with the lower assembly 204, with the pin elements 214 of the lower plate 206 seated in the recesses 216 formed in the upper plate 208 and the cylinder 212 is generally centered over the sample 207. 16 grams of 0.9% NaCl saline test solution is poured into the top of the cylinder 212 and allowed to flow down into the absorbent sample 207. A stopwatch is started when the first drop of solution contacts the sample 207 and is stopped when the liquid ring between the edge of the cylinder 212 and the sample 207 disappears. The reading on the stopwatch is recorded to two decimal places and represents the intake time (in seconds) required for the first insult to be taken into the absorbent sample 207.

A time period of 15 minutes is allowed to elapse, after which a second insult equal to the first insult is poured into the top of the cylinder 212 and again the intake time is measured as described above. After 15 minutes, the procedure is repeated for a third insult. An intake rate (in milliliters/second) for each of the three insults is determined by dividing the amount of solution used for each insult (16 grams) by the intake time measured for the corresponding insult.

At least three samples of each absorbent test are subjected to the FIR Test and the results are averaged to determine the intake rate.

Definitions

It should be noted that, when employed in the present disclosure, the terms "comprises," "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The term "absorbent article" generally refers to devices which can absorb and contain fluids. For example, personal care absorbent articles refer to devices which are placed against or near the skin to absorb and contain the various fluids discharged from the body.

The term "coform" is intended to describe a blend of meltblown fibers and cellulose fibers that is formed by air forming a meltblown polymer material while simultaneously blowing air-suspended cellulose fibers into the stream of meltblown fibers. The coform material may also include other materials, such as superabsorbent materials. The meltblown fibers containing wood fibers and/or other materials are collected on a forming surface, such as provided by a foraminous belt. The forming surface may include a gas-pervious material, such as spunbonded fabric material, that has been placed onto the forming surface.

The term "crosslinked" used in reference to the superabsorbent polymer refers to any means for effectively rendering normally water-soluble materials substantially water-insoluble but swellable. Such a crosslinking means can include, for example, physical entanglement, crystalline domains, covalent bonds, ionic complexes and associations, hydrophilic associations such as hydrogen bonding, hydrophobic associations, or Van der Waals forces.

The term "Darcy" is a CGS unit of permeability. One Darcy is the permeability of a solid through which one cubic centimeter of fluid, having a viscosity of one centipoise, will flow in one second through a section one centimeter thick and one square centimeter in cross-section, if the pressure difference between the two sides of the solid is one atmosphere. It turns out that permeability has the same units as area; since there is no SI unit of permeability, square meters are used. One Darcy is equal to about $0.98692 \times 10^{-12}$ m$^2$ or about $0.98692 \times 10^{-8}$ cm$^2$.

The term "disposable" is used herein to describe absorbent articles that are not intended to be laundered or otherwise restored or reused as an absorbent article after a single use. Examples of such disposable absorbent articles include, but are not limited to, personal care absorbent articles, health/medical absorbent articles, household/industrial absorbent articles, and sports/construction absorbent articles.

The term "dry superabsorbent polymer composition" generally refers to the superabsorbent polymer composition having less than about 10% moisture.

The terms "elastic," "elastomeric," "elastically", "extensible" and "elastically extensible" are used interchangeably to refer to a material or composite that generally exhibits properties which approximate the properties of natural rubber. The elastomeric material is generally capable of being extended or otherwise deformed, and then recovering a significant portion of its shape after the extension or deforming force is removed.

The terms "fluid impermeable," "liquid impermeable," "fluid impervious" and "liquid impervious" mean that fluid such as water or bodily fluids will not pass substantially through the layer or laminate under ordinary use conditions in a direction generally perpendicular to the plane of the layer or laminate at the point of fluid contact.

The term "health/medical absorbent articles" includes a variety of professional and consumer health-care products including, but not limited to, products for applying hot or cold therapy, medical gowns (i.e., protective and/or surgical gowns), surgical drapes, caps, gloves, face masks, bandages, wound dressings, wipes, covers, containers, filters, disposable garments and bed pads, medical absorbent garments, underpads, and the like.

The term "household/industrial absorbent articles" includes construction and packaging supplies, products for cleaning and disinfecting, wipes, covers, filters, towels, disposable cutting sheets, bath tissue, facial tissue, nonwoven roll goods, home-comfort products including pillows, pads, mats, cushions, masks and body care products such as products used to cleanse or treat the skin, laboratory coats, coveralls, trash bags, stain removers, topical compositions, pet care absorbent liners, laundry soil/ink absorbers, detergent agglomerators, lipophilic fluid separators, and the like.

The terms "hydrophilic" and "wettable" are used interchangeably to refer to a material having a contact angle of water in air of less than 90 degrees. The term "hydrophobic" refers to a material having a contact angle of water in air of at least 90 degrees. For the purposes of this application, contact angle measurements are determined as set forth in Robert J. Good and Robert J. Stromberg, Ed., in "Surface and Colloid Science—Experimental Methods," Vol. II, (Plenum Press, 1979), which is hereby incorporated by reference in a manner that is consistent herewith.

The term "layer" when used in the singular can have the dual meaning of a single element or a plurality of elements.

The term "mass median particle size" of a given sample of particles of superabsorbent polymer composition is defined as the particle size, which divides the sample in half on a mass basis, i.e., half of the sample by weight has a particle size greater than the mass median particle size, and half of the sample by mass has a particle size less than the mass median particle size. Thus, for example, the mass median particle size of a sample of superabsorbent polymer composition particles is 2 microns if one-half of the sample by weight is measured as more than 2 microns.

The term "MD" or "machine direction" refers to the orientation of the absorbent web that is parallel to the running direction of the forming fabric and generally within the plane formed by the forming surface. The term "CD" or "cross-machine direction" refers to the direction perpendicular to the MD and generally within the plane formed by the forming surface. Both MD and CD generally define a plane that is parallel to the forming surface. The term "ZD" or "Z-direction" refers to the orientation that is perpendicular to the plane formed by the MD and CD.

The term "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. In the particular case of a coform process, the meltblown fiber stream intersects with one or more material streams that are introduced from a different direction. Thereafter, the meltblown fibers and other materials are carried by the high velocity gas stream and are deposited on a collecting surface. The distribution and orientation of the meltblown fibers within the formed web is dependent on the geometry and process conditions. Under certain process and equipment conditions, the resulting fibers can be substantially "continuous," defined as having few separations, broken fibers or tapered ends when multiple fields of view are examined through a microscope at 10× or 20× magnification. When "continuous" melt blown fibers are produced, the sides of individual fibers will generally be parallel with minimal variation in fiber diameter within an individual fiber length. In contrast, under other conditions, the fibers can be overdrawn and strands can be broken and form a series of irregular, discrete fiber lengths and numerous broken ends. Retraction of the once attenuated broken fiber will often result in large clumps of polymer.

The terms "nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded-carded-web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

The term "personal care absorbent article" includes, but is not limited to, absorbent articles such as diapers, diaper pants, baby wipes, training pants, absorbent underpants, child care pants, swimwear, and other disposable garments; feminine care products including sanitary napkins, wipes, menstrual pads, menstrual pants, panty liners, panty shields, interlabials, tampons, and tampon applicators; adult-care products including wipes, pads such as breast pads, containers, incontinence products, and urinary shields; clothing components; bibs; athletic and recreation products; and the like.

The term "polymer" includes, but is not limited to, homopolymers, copolymers, for example, block, graft, random, and alternating copolymers, terpolymers, etc., and blends and modifications thereof. Furthermore, unless otherwise specifically limited, the term "polymer" shall include all possible configurational isomers of the material. These configurations include, but are not limited to isotactic, syndiotactic, and atactic symmetries.

The term "polyolefin" as used herein generally includes, but is not limited to, materials such as polyethylene, polypropylene, polyisobutylene, polystyrene, ethylene vinyl acetate copolymer and the like, the homopolymers, copolymers, terpolymers, etc., thereof, and blends and modifications thereof. The term "polyolefin" shall include all possible structures thereof, which includes, but is not limited to, isotatic, synodiotactic and random symmetries. Copolymers include random and block copolymers.

The term "sports/construction absorbent articles" includes headbands, wrist bands and other aids for absorption of perspiration, absorptive windings for grips and handles of sports equipment, and towels or absorbent wipes for cleaning and drying off equipment during use.

The terms "spunbond" and "spunbonded fiber" refer to fibers which are formed by extruding filaments of molten thermoplastic material from a plurality of fine, usually circular, capillaries of a spinneret, and then rapidly reducing the diameter of the extruded filaments.

The term "stretchable" refers to materials which may be extensible or which may be elastically extensible.

The term "superabsorbent" refers to water-swellable, water-insoluble organic or inorganic materials capable, under the most favorable conditions, of absorbing at least about 10 times their weight, or at least about 15 times their weight, or at least about 25 times their weight in an aqueous solution containing 0.9 weight percent sodium chloride.

The term "superabsorbent polymer composition" refers to a superabsorbent polymer comprising surface crosslinking and/or a surface additive.

The term "superabsorbent preproduct" refers to a material that is produced by conducting all of the steps for making a superabsorbent polymer as described herein, up to and including drying the material, and coarse grinding in a crusher, and removing particles greater than about 850 microns and smaller than about 150 microns.

The term "surface crosslinking" means that the level of functional crosslinks in the vicinity of the surface of the superabsorbent polymer particle generally is higher than the level of functional crosslinks in the interior of the superabsorbent polymer particle. As used herein, "surface" describes the outer-facing boundaries of the particle. For porous superabsorbent polymer particles, exposed internal surface also are included in the definition of surface.

The term "target zone" refers to an area of an absorbent core where it is particularly desirable for the majority of a fluid insult, such as urine, menses, or bowel movement, to initially contact. In particular, for an absorbent core with one or more fluid insult points in use, the insult target zone refers to the area of the absorbent core extending a distance equal to 15% of the total length of the composite from each insult point in both directions.

The term "thermoplastic" describes a material that softens when exposed to heat and which substantially returns to a non-softened condition when cooled to room temperature.

The term "% by weight" or "% wt" when used herein and referring to components of the superabsorbent polymer composition, is to be interpreted as based on the dry weight of the superabsorbent polymer composition, unless otherwise specified herein.

These terms may be defined with additional language in the remaining portions of the specification.

DETAILED DESCRIPTION

An absorbent article of the present invention can have a topsheet, a backsheet, and an absorbent core disposed between the topsheet and the backsheet. The absorbent core includes a superabsorbent polymer composition of the present invention.

Figure 8:
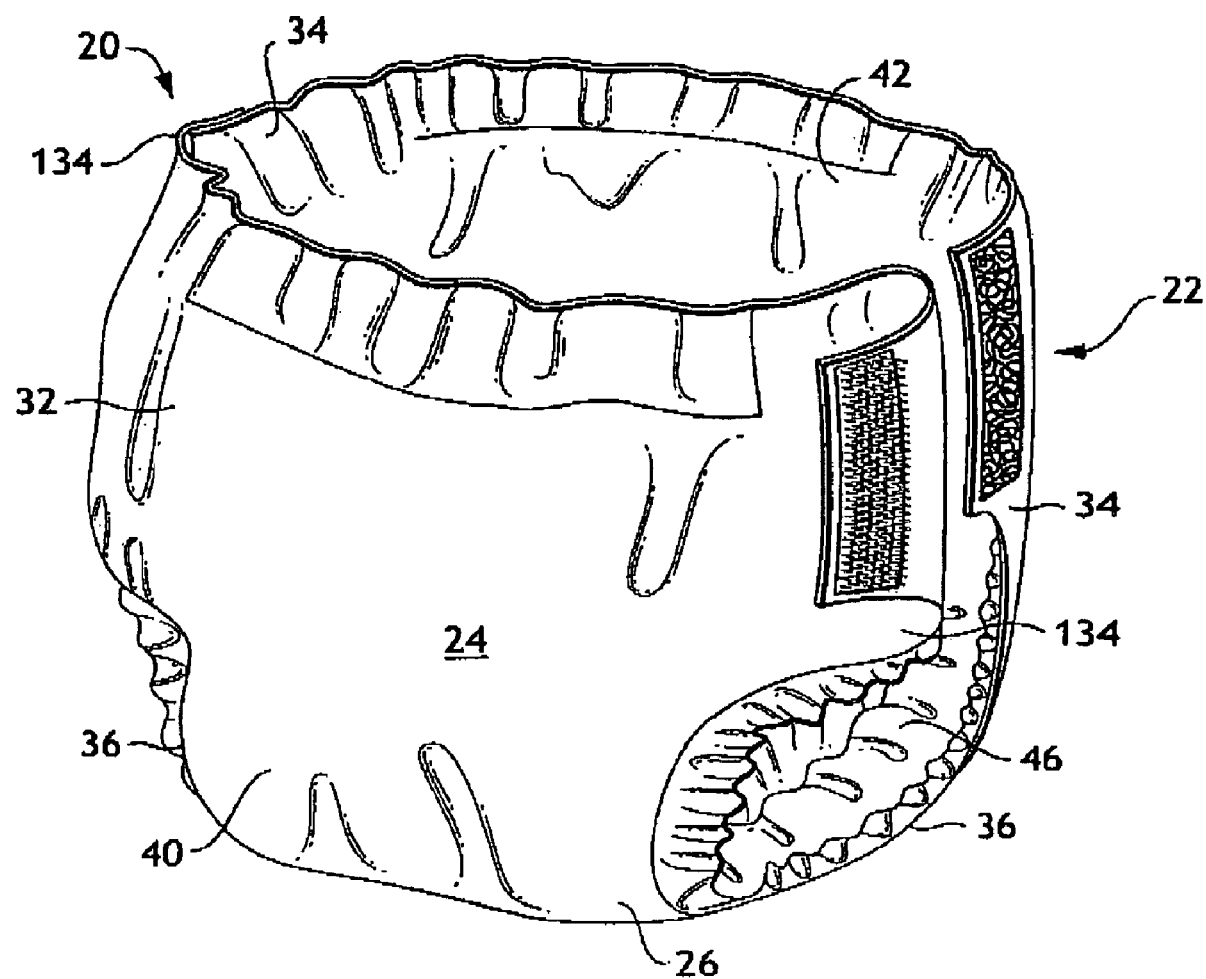
FIG. 8 is a perspective view of one embodiment of an absorbent article that may be made in accordance with the present invention.
Figure 9:
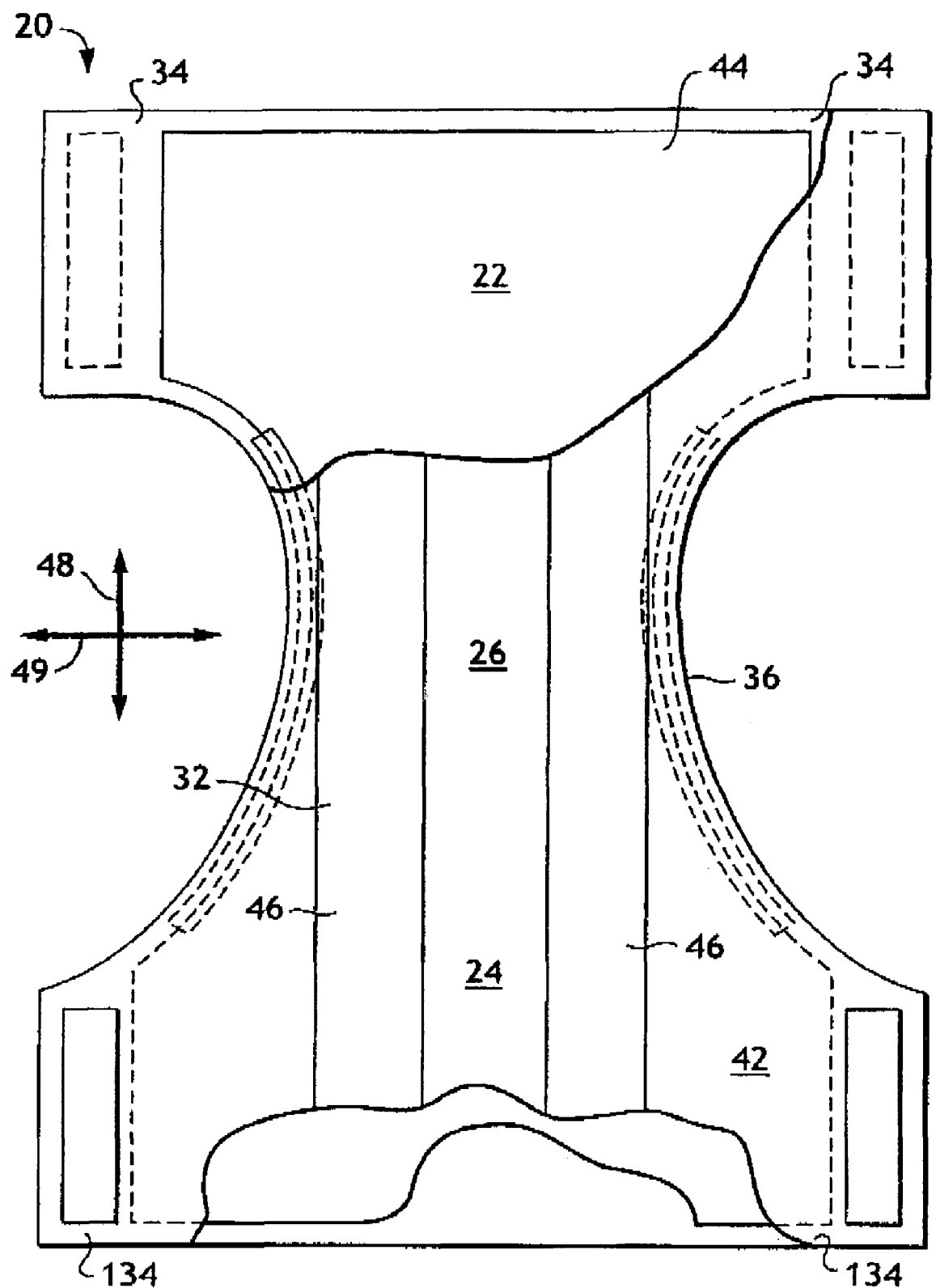
FIG. 9 is a plan view of the absorbent article shown in FIG. 8 with the article in an unfastened, unfolded and laid flat condition showing the surface of the article that faces the wearer when worn and with portions cut away to show underlying features.

To gain a better understanding of the present invention, attention is directed to FIG. 8 and FIG. 9 for exemplary purposes showing a training pant of the present invention. It is understood that the present invention is suitable for use with various other absorbent articles, including but not limited to other personal care absorbent articles, health/medical absorbent articles, household/industrial absorbent articles, sports/construction absorbent articles, and the like, without departing from the scope of the present invention.

Various materials and methods for constructing training pants are disclosed in PCT Patent Application WO 00/37009 published Jun. 29, 2000 by A. Fletcher et al.; U.S. Pat. No. 4,940,464 to Van Gompel et al.; U.S. Pat. No. 5,766,389 to Brandon et al., and U.S. Pat. No. 6,645,190 to Olson et al., all of which are incorporated herein by reference in a manner that is consistent herewith.

FIG. 8 illustrates a training pant in a partially fastened condition, and FIG. 9 illustrates a training pant in an opened and unfolded state. The training pant defines a longitudinal direction 48 that extends from the front of the training pant when worn to the back of the training pant. Perpendicular to the longitudinal direction 48 is a lateral direction 49.

The pair of training pants defines a front region 22, a back region 24, and a crotch region 26 extending longitudinally between and interconnecting the front and back regions. The pant also defines an inner surface adapted in use (e.g., positioned relative to the other components of the pant) to be disposed toward the wearer, and an outer surface opposite the inner surface. The training pant has a pair of laterally opposite side edges and a pair of longitudinally opposite waist edges.

The illustrated pant 20 may include a chassis 32, a pair of laterally opposite front side panels 34 extending laterally outward at the front region 22 and a pair of laterally opposite back side panels 134 extending laterally outward at the back region 24.

The chassis 32 includes a backsheet 40 and a topsheet 42 that may be joined to the backsheet 40 in a superimposed relation therewith by adhesives, ultrasonic bonds, thermal bonds or other conventional techniques. The chassis 32 may further include an absorbent core 44 such as shown in FIG. 9 disposed between the backsheet 40 and the topsheet 42 for absorbing fluid body exudates exuded by the wearer, and may further include a pair of containment flaps 46 secured to the topsheet 42 or the absorbent core 44 for inhibiting the lateral flow of body exudates.

The backsheet 40, the topsheet 42 and the absorbent core 44 may be made from many different materials known to those skilled in the art. All three layers, for instance, may be extensible and/or elastically extensible. Further, the stretch properties of each layer may vary in order to control the overall stretch properties of the product.

The backsheet 40, for instance, may be breathable and/or may be fluid impermeable. The backsheet 40 may be constructed of a single layer, multiple layers, laminates, spunbond fabrics, films, meltblown fabrics, elastic netting, microporous webs or bonded-carded-webs. The backsheet 40, for instance, can be a single layer of a fluid impermeable material, or alternatively can be a multi-layered laminate structure in which at least one of the layers is fluid impermeable.

The backsheet 40 can be biaxially extensible and optionally biaxially elastic. Elastic non-woven laminate webs that can be used as the backsheet 40 include a non-woven material joined to one or more gatherable non-woven webs or films. Stretch Bonded Laminates (SBL) and Neck Bonded Laminates (NBL) are examples of elastomeric composites.

Examples of suitable nonwoven materials are spunbond-meltblown fabrics, spunbond-meltblown-spunbond fabrics, spunbond fabrics, or laminates of such fabrics with films, or other nonwoven webs. Elastomeric materials may include cast or blown films, meltblown fabrics or spunbond fabrics composed of polyethylene, polypropylene, or polyolefin elastomers, as well as combinations thereof. The elastomeric materials may include PEBAX elastomer (available from AtoFina Chemicals, Inc., a business having offices located in Philadelphia, Pa. U.S.A.), HYTREL elastomeric polyester (available from Invista, a business having offices located in Wichita, Kans. U.S.A.), KRATON elastomer (available from Kraton Polymers, a business having offices located in Houston, Tex., U.S.A.), or strands of LYCRA elastomer (available from Invista), or the like, as well as combinations thereof. The backsheet 40 may include materials that have elastomeric properties through a mechanical process, printing process, heating process or chemical treatment. For example, such materials may be apertured, creped, neck-stretched, heat activated, embossed, and micro-strained, and may be in the form of films, webs, and laminates.

One example of a suitable material for a biaxially stretchable backsheet 40 is a breathable elastic film/nonwoven laminate, such as described in U.S. Pat. No. 5,883,028, to Morman et al., incorporated herein by reference in a manner that is consistent herewith. Examples of materials having two-way stretchability and retractability are disclosed in U.S. Pat. Nos. 5,116,662 to Morman and U.S. Pat. No. 5,114,781 to Morman, each of which is incorporated herein by reference in a manner that is consistent herewith. These two patents describe composite elastic materials capable of stretching in at least two directions. The materials have at least one elastic sheet and at least one necked material, or reversibly necked material, joined to the elastic sheet at least at three locations arranged in a nonlinear configuration, so that the necked, or reversibly necked, web is gathered between at least two of those locations.

The topsheet 42 is suitably compliant, soft-feeling and non-irritating to the wearer's skin. The topsheet 42 is also sufficiently liquid permeable to permit liquid body exudates to readily penetrate through its thickness to the absorbent core 44. A suitable topsheet 42 may be manufactured from a wide selection of web materials, such as porous foams, reticulated foams, apertured plastic films, woven and non-woven webs, or a combination of any such materials. For example, the topsheet 42 may include a meltblown web, a spunbonded web, or a bonded-carded-web composed of natural fibers, synthetic fibers or combinations thereof. The topsheet 42 may be composed of a substantially hydrophobic material, and the hydrophobic material may optionally be treated with a surfactant or otherwise processed to impart a desired level of wettability and hydrophilicity.

The topsheet 42 may also be extensible and/or elastomerically extensible. Suitable elastomeric materials for construction of the topsheet 42 can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon, a business having offices located in Cleveland, Ohio U.S.A.), or PEBAX elastomers. The topsheet 42 can also be made from extensible materials such as those described in U.S. Pat. No. 6,552,245 to Roessler et al. which is incorporated herein by reference in a manner that is consistent herewith. The topsheet 42 can also be made from biaxially stretchable materials as described in U.S. Pat. No. 6,641,134 filed to Vukos et al. which is incorporated herein by reference in a manner that is consistent herewith.

The article 20 can optionally further include a surge management layer which may be located adjacent the absorbent core 44 and attached to various components in the article 20 such as the absorbent core 44 or the topsheet 42 by methods known in the art, such as by using an adhesive. In general, a surge management layer helps to quickly acquire and diffuse surges or gushes of liquid that may be rapidly introduced into the absorbent structure of the article. The surge management layer can temporarily store the liquid prior to releasing it into the storage or retention portions of the absorbent core 44. Examples of suitable surge management layers are described in U.S. Pat. Nos. 5,486,166 to Bishop et al.; U.S. Pat. No. 5,490,846 to Ellis et al.; and U.S. Pat. No. 5,820,973 to Dodge et al., each of which is incorporated herein by reference in a manner that is consistent herewith.

The article 20 can further comprise an absorbent core 44. The absorbent core 44 may have any of a number of shapes. For example, it may have a 2-dimensional or 3-dimensional configuration, and may be rectangular shaped, triangular shaped, oval shaped, race-track shaped, I-shaped, generally hourglass shaped, T-shaped and the like. It is often suitable for the absorbent core 44 to be narrower in the crotch portion 26 than in the rear 24 or front 22 portion(s). The absorbent core 44 can be attached in an absorbent article, such as to the backsheet 40 and/or the topsheet 42 for example, by bonding means known in the art, such as ultrasonic, pressure, adhesive, aperturing, heat, sewing thread or strand, autogenous or self-adhering, hook-and-loop, or any combination thereof.

In some aspects, the absorbent core 44 can have a significant amount of stretchability. For example, the absorbent core 44 can comprise a matrix of fibers which includes an operative amount of elastomeric polymer fibers. Other methods known in the art can include attaching superabsorbent polymer particles to a stretchable film, utilizing a nonwoven substrate having cuts or slits in its structure, and the like.

The absorbent core 44 can be formed using methods known in the art. While not being limited to the specific method of manufacture, the absorbent core can utilize a meltblown process and can further be formed on a coform line. Exemplary meltblown processes are described in various patents and publications, including NRL Report 4364, "Manufacture of Super-Fine Organic Fibers" by V. A. Wendt, E. L. Boone and C. D. Fluharty; NRL Report 5265, "An Improved Device For the Formation of Super-Fine Thermoplastic Fibers" by K. D.

Lawrence, R. T. Lukas and J. A. Young; and U.S. Pat. No. 3,849,241 to Butin et al. and U.S. Pat. No. 5,350,624 to Georger et al., all of which are incorporated herein by reference in a manner that is consistent herewith.

To form "coform" materials, additional components are mixed with the meltblown fibers as the fibers are deposited onto a forming surface. For example, the superabsorbent polymer composition of the present invention and fluff, such as wood pulp fibers, may be injected into the meltblown fiber stream so as to be entrapped and/or bonded to the meltblown fibers. Exemplary coform processes are described in U.S. Pat. No. 4,100,324 to Anderson et al.; U.S. Pat. No. 4,587,154 to Hotchkiss et al.; U.S. Pat. No. 4,604,313 to McFarland et al.; U.S. Pat. No. 4,655,757 to McFarland et al.; U.S. Pat. No. 4,724,114 to McFarland et al.; U.S. Pat. No. 4,100,324 to Anderson et al.; and U.K. Patent GB 2,151,272 to Minto et al., each of which is incorporated herein by reference in a manner that is consistent herewith. Absorbent, elastomeric meltblown webs containing high amounts of superabsorbent are described in U.S. Pat. No. 6,362,389 to D. J. McDowall, and absorbent, elastomeric meltblown webs containing high amounts of superabsorbent and low superabsorbent shakeout values are described in pending U.S. patent application Ser. No. 10/883,174 to X. Zhang et al., each of which is incorporated herein by reference in a manner that is consistent herewith.

Figure 10:
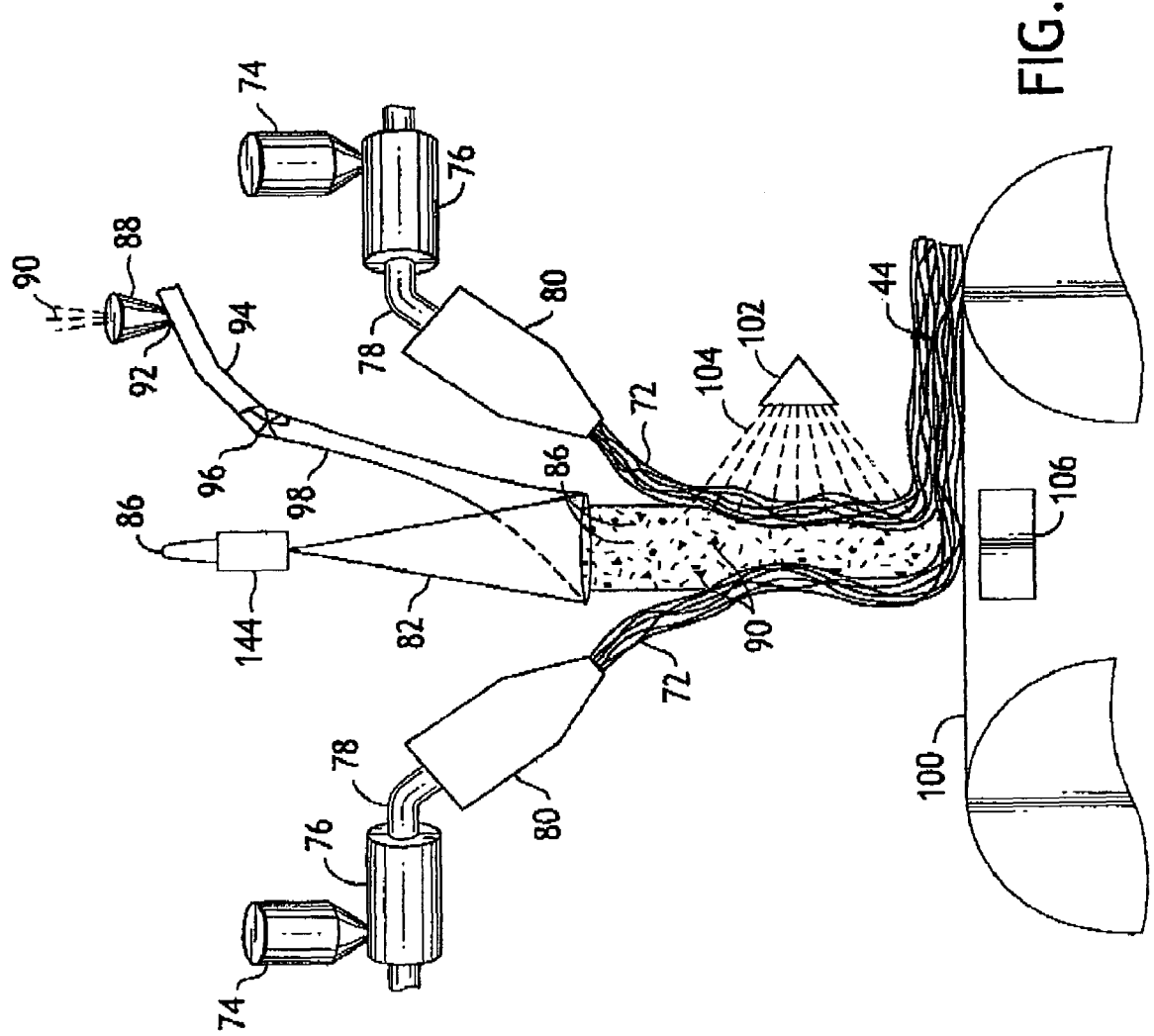
FIG. 10 is a schematic diagram of one version of a method and apparatus for producing an absorbent core.

One example of a method of forming an absorbent core 44 for use in the present invention is illustrated in FIG. 10. The dimensions of the apparatus in FIG. 10 are described herein by way of example. Other types of apparatus having different dimensions and/or different structures may also be used to form the absorbent core 44. As shown in FIG. 10, elastomeric material 72 in the form of pellets can be fed through two pellet hoppers 74 into two single screw extruders 76 that each feed a spin pump 78. The elastomeric material 72 may be a multicomponent elastomer blend available under the trade designation VISTMAXX 2370 from ExxonMobil Chemical Company (a business having offices located in Houston, Tex., U.S.A.), as well as others mentioned herein. Each spin pump 78 feeds the elastomeric material 72 to a separate meltblown die 80. Each meltblown die 80 may have 30 holes per inch (hpi). The die angle may be adjusted anywhere between 0 and 70 degrees from horizontal, and is suitably set at about 45 degrees. The forming height may be at a maximum of about 16 inches, but this restriction may differ with different equipment.

A chute 82 having a width of about 24 inches (61 cm) wide may be positioned between the meltblown dies 80. The depth, or thickness, of the chute 82 may be adjustable in a range from about 0.5 to about 1.25 inches (1.3 cm to 3.2 cm), or from about 0.75 to about 1.0 inch (1.9 cm to 2.5 cm). A picker 144 connects to the top of the chute 82. The picker 144 is used to fiberize the pulp fibers 86. The picker 144 may be limited to processing low strength or debonded (treated) pulps, in which case the picker 144 may limit the illustrated method to a very small range of pulp types. In contrast to conventional hammermills that use hammers to impact the pulp fibers repeatedly, the picker 144 uses small teeth to tear the pulp fibers 86 apart. Suitable pulp fibers 86 for use in the method illustrated in FIG. 10 include those mentioned herein, such as NB480 (available from Weyerhaeuser Co., a business having offices located in Federal Way, Wash., U.S.A.).

At an end of the chute 82 opposite the picker 144 is a superabsorbent polymer feeder 88. The feeder 88 pours the superabsorbent polymer composition 90 of the present invention into a hole 92 in a pipe 94 which then feeds into a blower fan 96. Past the blower fan 96 is a length of 4-inch (10-cm) diameter pipe 98 sufficient for developing a fully developed turbulent flow at about 5,000 feet per minute, which allows the superabsorbent polymer composition particles 90 to become distributed. The pipe 98 widens from a 4-inch diameter to the 24-inch by 0.75-inch (61 cm by 1.9 cm) chute 82, at which point the superabsorbent polymer composition 90 mixes with the pulp fibers 86 and the mixture falls straight down and gets mixed on either side at an approximately 45-degree angle with the elastomeric material 72. The mixture of superabsorbent polymer composition 90, pulp fibers 86, and elastomeric material 72 falls onto a wire conveyor 100 moving from about 14 to about 35 feet per minute. However, before hitting the wire conveyor 100, a spray boom 102 optionally sprays an aqueous surfactant mixture 104 in a mist through the mixture, thereby rendering the resulting absorbent core 44 wettable. The surfactant mixture 104 may be a 1:3 mixture of GLUCOPON 220 UP (available from Cognis Corporation having a place of business in Cincinnati, Ohio, U.S.A.) and AHCOVEL Base N-62 (available from Uniqema, having a place of business in New Castle, Del., U.S.A.). An under wire vacuum 106 is positioned beneath the conveyor 100 to assist in forming the absorbent core 44.

Figure 11:
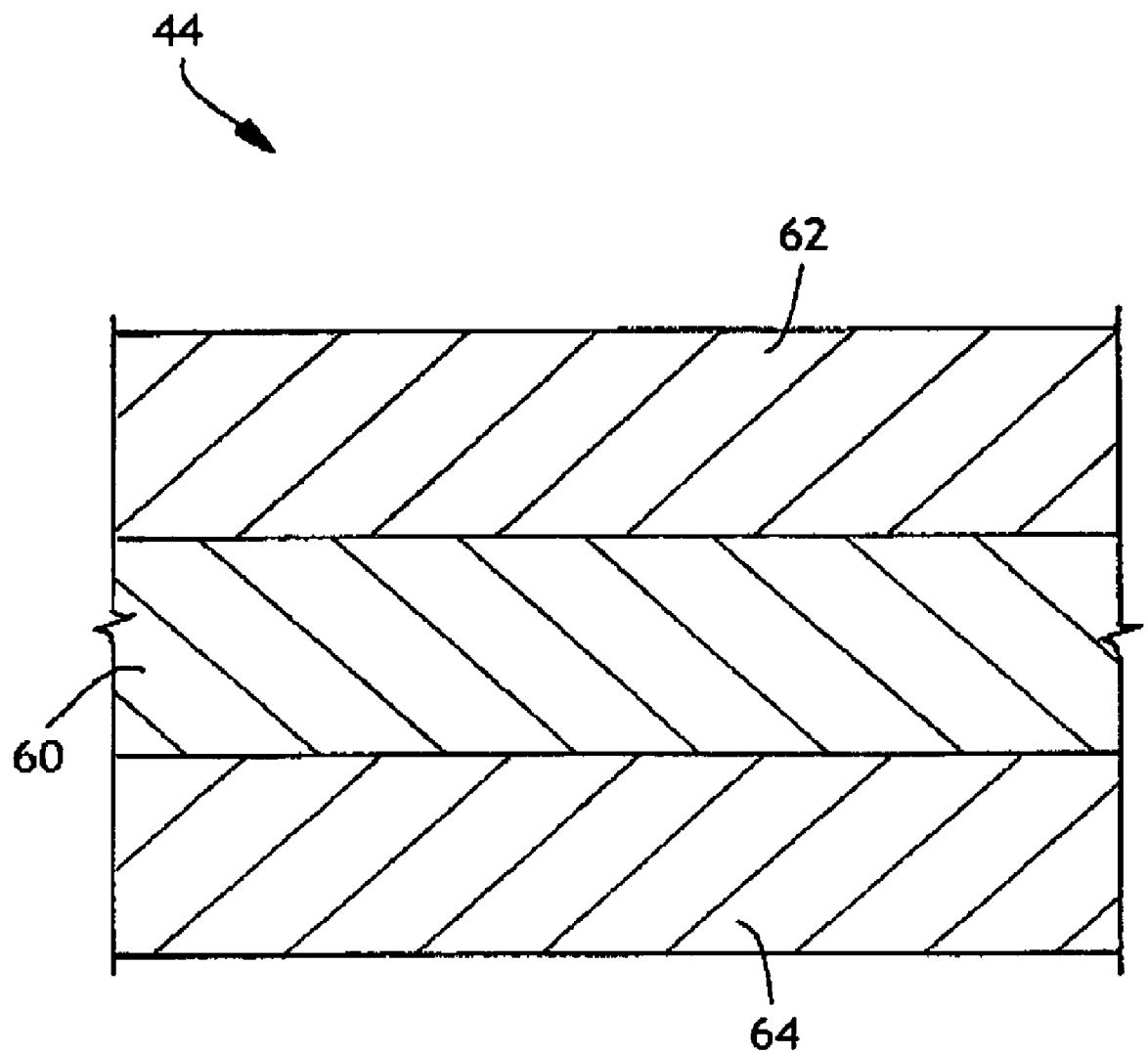
FIG. 11 is a cross-sectional side view of a layered absorbent core according to the present invention.

In general, the absorbent core 44 is often a unitary structure comprising a substantially uniform distribution of superabsorbent polymer composition particles, fibers, and any other optional additives. However, referring to FIG. 11, in some aspects, the absorbent core 44 may be further enhanced through structural modifications when combined with superabsorbent polymer composition of the present invention. For example, providing a layer 60 comprising substantially superabsorbent polymer composition particles of the present invention sandwiched between layers 62 and 64 comprising substantially fluff fibers, such as NB480, or other natural or synthetic fibers can result in an absorbent core having improved absorbent properties, such as fluid insult intake rate, when compared to a structure comprising a substantially uniform distribution of the superabsorbent polymer composition and fluff fibers. Such layering can occur in the z-direction of the absorbent core and may optionally cover the entire x-y area. However, the layers 60, 62 and 64 need not be discreet from one another. For example, in some aspects, the z-directional middle portion 60 of the absorbent core need only contain a higher superabsorbent polymer particles percentage (e.g., at least about 10% by weight higher) than the top layer 62 and/or bottom layer 64 of the absorbent core. Desirably, the layers are present in the area of the absorbent core that is within an insult target zone.

As referenced above, the absorbent core 44 also includes absorbent material, such as the superabsorbent polymer composition and/or fluff. Additionally, the superabsorbent polymer composition can be operatively contained within a matrix of fibers, such as polymeric fibers. Accordingly, the absorbent core 44 can comprise a quantity of superabsorbent polymer composition and/or fluff contained within a matrix of fibers. In some aspects, the amount of superabsorbent polymer composition in the absorbent core 44 can be at least about 10% by weight of the core, such as at least about 30%, or at least about 60% by weight or at least about 90%, or between about 10% and about 99% by weight of the core, or between about 30% to about 90% by weight of the core to provide improved benefits. Optionally, the amount of superabsorbent polymer composition can be at least about 95% by weight of the core. In other aspects, the absorbent core 44 can comprise about 35% or less by weight fluff, such as about 20% or less, or 10% or less by weight fluff.

It should be understood that the present invention is not restricted to use with the superabsorbent polymer composition and/or fluff. In some aspects, the absorbent core 44 may additionally or alternatively include materials such as surfactants, ion exchange resin particles, moisturizers, emollients, perfumes, natural fibers, synthetic fibers, fluid modifiers, odor control additives, and combinations thereof. Alternatively, the absorbent core 44 can include a foam.

In order to function well, the absorbent core 44 can have certain desired properties to provide improved performance as well as greater comfort and confidence among the user. For instance, the absorbent core 44 can have corresponding configurations of absorbent capacities, densities, basis weights and/or sizes which are selectively constructed and arranged to provide desired combinations of absorbency properties such as liquid intake rate, absorbent capacity, liquid distribution or fit properties such as shape maintenance and aesthetics. Likewise, the components can have desired wet to dry strength ratios, mean flow pore sizes, permeabilities and elongation values.

As mentioned above, the absorbent core 44 can optionally include elastomeric polymer fibers. The elastomeric material of the polymer fibers may include an olefin elastomer or a non-olefin elastomer, as desired. For example, the elastomeric fibers can include olefinic copolymers, polyethylene elastomers, polypropylene elastomers, polyester elastomers, polyisoprene, cross-linked polybutadiene, diblock, triblock, tetrablock, or other multi-block thermoplastic elastomeric and/or flexible copolymers such as block copolymers including hydrogenated butadiene-isoprene-butadiene block copolymers; stereoblock polypropylenes; graft copolymers, including ethylene-propylene-diene terpolymer or ethylene-propylene-diene monomer (EPDM) rubber, ethylene-propylene random copolymers (EPM), ethylene propylene rubbers (EPR), ethylene vinyl acetate (EVA), and ethylene-methyl acrylate (EMA); and styrenic block copolymers including diblock and triblock copolymers such as styrene-isoprene-styrene (SIS), styrene-butadiene-styrene (SBS), styrene-isoprene-butadiene-styrene (SIBS), styrene-ethylene/butylene-styrene (SEBS), or styrene-ethylene/propylene-styrene (SEPS), which may be obtained from Kraton Inc. under the trade designation KRATON elastomeric resin or from Dexco, a division of ExxonMobil Chemical Company under the trade designation VECTOR (SIS and SBS polymers); blends of thermoplastic elastomers with dynamic vulcanized elastomer-thermoplastic blends; thermoplastic polyether ester elastomers; ionomeric thermoplastic elastomers; thermoplastic elastic polyurethanes, including those available from Invista Corporation under the trade name LYCRA polyurethane, and ESTANE available from Noveon, Inc., a business having offices located in Cleveland, Ohio, U.S.A.; thermoplastic elastic polyamides, including polyether block amides available from AtoFina Chemicals, Inc. (a business having offices located in Philadelphia, Pa., U.S.A.) under the trade name PEBAX; polyether block amide; thermoplastic elastic polyesters, including those available from E. I. Du Pont de Nemours Co., under the trade name HYTREL, and ARNITEL from DSM Engineering Plastics (a business having offices located in Evansville, Ind., U.S.A.) and single-site or metallocene-catalyzed polyolefins having a density of less than about 0.89 grams/cubic centimeter, available from Dow Chemical Co. (a business having offices located in Freeport, Tex., U.S.A.) under the trade name AFFINITY; and combinations thereof.

As used herein, a tri-block copolymer has an ABA structure where the A represents several repeat units of type A, and B represents several repeat units of type B. As mentioned above, several examples of styrenic block copolymers are SBS, SIS, SIBS, SEBS and SEPS. In these copolymers the A blocks are polystyrene and the B blocks are a rubbery component. Generally, these triblock copolymers have molecular weights that can vary from the low thousands to hundreds of thousands, and the styrene content can range from 5% to 75% based on the weight of the triblock copolymer. A diblock copolymer is similar to the triblock, but is of an AB structure. Suitable diblocks include styrene-isoprene diblocks, which have a molecular weight of approximately one-half of the triblock molecular weight having the same ratio of A blocks to B blocks.

In desired arrangements, the polymer fibers can include at least one material selected from the group consisting of styrenic block copolymers, elastic polyolefin polymers and co-polymers and EVA/EMA type polymers.

In some particular arrangements, for example, the elastomeric material of the polymer fibers can include various commercial grades of low crystallinity, lower molecular weight metallocene polyolefins, available from ExxonMobil Chemical Company (a company having offices located in Houston, Tex., U.S.A.) under the VISTAMAXX trade designation. Some VISTAMAXX materials are believed to be metallocene propylene ethylene co-polymer. For example, in one aspect the elastomeric polymer can be VISTAMAXX PLTD 2210. In other aspects, the elastomeric polymer can be VISTAMAXX PLTD 1778. In a particular aspect, the elastomeric polymer is VISTAMAXX 2370. Another optional elastomeric polymer is KRATON blend G 2755 from Kraton Inc. The KRATON material is believed to be a blend of styrene ethylene-butylene styrene polymer, ethylene waxes and tackifying resins.

In some aspects, the elastomeric polymer fibers can be produced from a polymer material having a selected melt flow rate (MFR). In a particular aspect, the MFR can be up to a maximum of about 300. Alternatively, the MFR can be up to about 230 or 250. In another aspect, the MFR can be a minimum of not less than about 9, or not less than 20. The MFR can alternatively be not less than about 50 to provide desired performance. The described melt flow rate has the units of grams flow per 10 minutes (g/10 min). The parameter of melt flow rate is well known, and can be determined by conventional techniques, such as by employing test ASTM D 1238 70 "extrusion plastometer" Standard Condition "L" at 230° C. and 2.16 kg applied force.

As referenced above, the polymer fibers of the absorbent core 44 can include an amount of a surfactant. The surfactant can be combined with the polymer fibers of the absorbent core in any operative manner. Various techniques for combining the surfactant are conventional and well known to persons skilled in the art. For example, the surfactant may be compounded with the polymer employed to form a meltblown fiber structure. In a particular feature, the surfactant may be configured to operatively migrate or segregate to the outer surface of the fibers upon the cooling of the fibers. Alternatively, the surfactant may be applied to or otherwise combined with the polymer fibers after the fibers have been formed.

The polymer fibers can include an operative amount of surfactant, based on the total weight of the fibers and surfactant. In some aspects, the polymer fibers can include at least a minimum of about 0.1% by weight surfactant, as determined by water extraction. The amount of surfactant can alternatively be at least about 0.15% by weight, and can optionally be at least about 0.2% by weight to provide desired benefits. In other aspects, the amount of surfactant can be generally not more than a maximum of about 2% by weight, such as not more than about 1% by weight, or not more than about 0.5% by weight to provide improved performance.

If the amount of surfactant is outside the desired ranges, various disadvantages can occur. For example, an excessively low amount of surfactant may not allow fibers, such as hydrophobic meltblown fibers, to wet with the absorbed fluid. In contrast, an excessively high amount of surfactant may allow the surfactant to wash off from the fibers and undesirably interfere with the ability of the absorbent core to transport fluid, or may adversely affect the attachment strength of the absorbent core to the absorbent article. Where the surfactant is compounded or otherwise internally added to the polymer fibers, an excessively high level of surfactant can create conditions that cause poor formation of the polymer fibers and interfiber bonds.

In some configurations, the surfactant can include at least one material selected from the group that includes polyethylene glycol ester condensates and alkyl glycoside surfactants. For example, the surfactant can be a GLUCOPON surfactant, available from Cognis Corporation, which can be composed of 40% water, and 60% d-glucose, decyl, octyl ethers and oligomerics.

In other aspects of the invention, the surfactant can be in the form of a sprayed-on surfactant comprising a water/surfactant solution which includes 16 liters of hot water (about 45° C. to 50° C.) mixed with 0.20 kg of GLUCOPON 220 UP surfactant available from Cognis Corporation and 0.36 kg of AHCHOVEL Base N-62 surfactant available from Uniqema. When employing a sprayed-on surfactant, a relatively lower amount of sprayed-on surfactant may be desirable to provide the desired containment of the superabsorbent polymer particles. Excessive amounts of the fluid surfactant may hinder the desired attachment of the superabsorbent polymer particles to the molten, elastomeric meltblown fibers, for example.

An example of an internal surfactant or wetting agent that can be compounded with the elastomeric fiber polymer can include a MAPEG DO 400 PEG (polyethylene glycol) ester, available from BASF (a business having offices located in Freeport, Tex., U.S.A.). Other internal surfactants can include a polyether, a fatty acid ester, a soap or the like, as well as combinations thereof.

As referenced above, the absorbent core 44 can optionally include fluff, such as cellulosic fibers. Such cellulosic fibers may include, but are not limited to, chemical wood pulps such as sulfite and sulfate (sometimes called Kraft) pulps, as well as mechanical pulps such as ground wood, thermomechanical pulp and chemithermomechanical pulp. More particularly, the pulp fibers may include cotton, other typical wood pulps, cellulose acetate, debonded chemical wood pulp, and combinations thereof. Pulps derived from both deciduous and coniferous trees can be used. Additionally, the cellulosic fibers may include such hydrophilic materials as natural plant fibers, milkweed floss, cotton fibers, microcrystalline cellulose, microfibrillated cellulose, or any of these materials in combination with wood pulp fibers. Suitable cellulosic fluff fibers can include, for example, NB480 (available from Weyerhaeuser Co.); NB416, a bleached southern softwood Kraft pulp (available from Weyerhaeuser Co.); CoosAbsorb S, a bleached southern softwood Kraft pulp (available from Bowater Inc., a business having offices located in Greenville, S.C. U.S.A.).; SULPHATATE HJ, a chemically modified hardwood pulp (available from Rayonier Inc., a business having offices located in Jesup, Ga., U.S.A.); NF 405, a chemically treated bleached southern softwood Kraft pulp (available from Weyerhaeuser Co.); and CR 1654, a mixed bleached southern softwood and hardwood Kraft pulp (available from Bowater Inc.)

As referenced above, the absorbent core 44 also includes a desired amount of the superabsorbent polymer composition of the present invention. In general, superabsorbent polymers (SAPs) typically are polymers of unsaturated carboxylic acids or derivatives thereof. These polymers may be rendered water insoluble, but water swellable, by crosslinking the polymer with a di- or polyfunctional internal crosslinking agent. These internally crosslinked polymers are at least partially neutralized and contain pendant anionic carboxyl groups on the polymer backbone that enable the polymer to absorb aqueous fluids, such as body fluids.

SAPs are manufactured by known polymerization techniques, such as by polymerization in aqueous solution by gel polymerization. The result of this polymerization process is a polymer with superabsorbent properties, which can then be reduced in size to small particles by mechanical forces and dried using drying procedures and apparatus known in the art. The drying process can be followed by pulverization of the resulting particles to the desired particle size. In general, particles too small in size swell after absorbing a fluid and can block the absorption of further fluid, while particles too large in size have a reduced surface area which can decrease the rate of absorption.

To improve the fluid absorption profile, the particles may be optimized with respect to one or more of absorption capacity, absorption rate, acquisition time, and/or permeability. Optimization allows a reduction in the amount of fluff fiber in an absorbent article, which results in a thinner article. However, it generally can be difficult to impossible to maximize all of these absorption profile properties simultaneously.

It may be desirable to subject a superabsorbent polymer to a post-treatment to crosslink the pendant anionic carboxyl groups on the surface of the particles and/or to impart a coating onto the surface of the particles to form superabsorbent polymer composition particles. For example, some aspects of the present invention include a superabsorbent polymer composition comprising superabsorbent polymer particles that have been surface treated with a surface additive comprising from about 0.01% to about 2% by weight of an inorganic metal compound, based on the superabsorbent polymer composition. In some aspects, the superabsorbent polymer composition exhibits a centrifuge retention capacity of at least about 30 g/g as measured by the Centrifuge Retention Capacity Test and a free swell gel bed permeability of at least 10 Darcy as measured by the Free Swell Gel Bed Permeability.

Other aspects of the present invention include a superabsorbent polymer composition comprising:

a) from about 55% to about 99.9% by weight of polymerizable unsaturated acid-group-containing-monomers based on the superabsorbent polymer composition; and b) from about 0.001% to about 5% by weight of internal crosslinking agent based on the polymerizable unsaturated acid-group-containing-monomer, wherein the superabsorbent polymer has a degree of neutralization of greater than about 25%, wherein elements a) and b) are polymerized and prepared into superabsorbent polymer particles further comprising the following surface additives to form surface-treated superabsorbent polymer particles:

i) from about 0.001% to about 5% by weight of surface crosslinking agent based on the dry superabsorbent polymer composition;

ii) from about 0.01% to about 2% by weight of a water-insoluble inorganic metal compound based on the dry superabsorbent polymer composition; and iii) from 0% to about 5% by weight of a polymeric coating based on the dry superabsorbent polymer composition. The surface treated superabsorbent polymer particles may additionally be heat-treated. In some aspects, the superabsorbent polymer composition exhibits a centrifuge retention capacity of at least about 30 g/g as measured by the Centrifuge Retention Capacity Test and a free swell gel bed permeability of at least 10 Darcy as measured by the Free Swell Gel Bed Permeability.

Still other aspects of the present invention include a superabsorbent polymer composition comprising superabsorbent polymer particles that have been treated with a finely-divided, water-insoluble inorganic metal salt comprising the steps of: a) providing superabsorbent polymer particles; b) preparing a first solution of a first inorganic metal salt; c) adding to and mixing with the first solution of b) a second solution of a second inorganic metal salt, wherein the first solution and second solution react on mixing to precipitate a third water-insoluble metal salt to form a water-insoluble metal salt slurry; d) optionally oxidizing the metal of the water-insoluble metal salt slurry to a higher valence state; and e) applying the water-insoluble metal salt slurry to the superabsorbent polymer particles without isolation and drying of the water-insoluble metal salt slurry.

Yet other aspects of the present invention include a superabsorbent polymer composition comprising superabsorbent polymer particles that have been treated with finely-divided, water-insoluble inorganic metal salt comprising the steps of: a) providing superabsorbent polymer particles; b) preparing a first solution of a first inorganic metal salt; c) preparing a second solution of a second inorganic metal salt; d) applying the first solution and second solution to the superabsorbent polymer particles to form a water-insoluble inorganic metal salt precipitate directly on or in the vicinity of a surface of the superabsorbent polymer particles.

A superabsorbent polymer as set forth in some aspects of the present invention is obtained by the initial polymerization of from about 55% to about 99.9% by weight of a polymerizable unsaturated acid-group-containing-monomer, based on the superabsorbent polymer. A suitable monomer includes any of those containing carboxyl groups, such as acrylic acid, methacrylic acid, or 2-acrylamido-2-methylpropanesulfonic acid, or mixtures thereof. Suitably, at least about 50% by weight, such as at least about 75% by weight of the acid groups, are carboxyl groups.

The acid groups can be neutralized to the extent of at least about 25 mol %, that is, the acid groups are desirably present as sodium, potassium, or ammonium salts. In some aspects, the degree of neutralization may be at least about 50 mol %. In some aspects, it is desirable to utilize polymers obtained by polymerization of acrylic acid or methacrylic acid, the carboxyl groups of which are neutralized to the extent of from about 50 mol % to about 80 mol %, in the presence of internal crosslinking agents.

In some aspects, the suitable monomer that can be copolymerized with the ethylenically unsaturated monomer may include, but is not limited to, acrylamide, methacrylamide, hydroxyethyl acrylate, dimethylaminoalkyl(meth)-acrylate, ethoxylated (meth)-acrylates, dimethylaminopropylacrylamide, or acrylamidopropyltrimethylammonium chloride. Such monomer may be present in a range of from 0% to about 40% by weight of the copolymerized monomer.

The superabsorbent polymer composition of the present invention suitably also includes internal crosslinking agents. The internal crosslinking agent has at least two ethylenically unsaturated double bonds, or one ethylenically unsaturated double bond and one functional group that is reactive toward acid groups of the polymerizable unsaturated acid-group-containing-monomer, or several functional groups that are reactive towards acid groups can be used as the internal crosslinking component and is desirably present during the polymerization of the polymerizable unsaturated acid-group-containing-monomer.

Examples of internal crosslinking agents include, but are not limited to, aliphatic unsaturated amides, such as methylenebisacryl- or -methacrylamide or ethylenebisacrylamide; aliphatic esters of polyols or alkoxylated polyols with ethylenically unsaturated acids, such as di(meth)acrylates or tri (meth)acrylates of butanediol or ethylene glycol, polyglycols or trimethylolpropane; di- and triacrylate esters of trimethylolpropane which may be oxyalkylated, desirably ethoxylated, with about 1 to about 30 moles of alkylene oxide; acrylate and methacrylate esters of glycerol and pentaerythritol and of glycerol and pentaerythritol oxyethylated with desirably about 1 to about 30 moles of ethylene oxide; allyl compounds, such as allyl (meth)acrylate, alkoxylated allyl (meth)acrylate reacted with desirably about 1 to about 30 moles of ethylene oxide, triallyl cyanurate, triallyl isocyanurate, maleic acid diallyl ester, poly-allyl esters, tetraallyloxyethane, triallylamine, tetraallylethylenediamine, diols, polyols, hydroxy allyl or acrylate compounds and allyl esters of phosphoric acid or phosphorous acid; and monomers that are capable of crosslinking, such as N-methylol compounds of unsaturated amides, such as of methacrylamide or acrylamide, and the ethers derived therefrom. Ionic crosslinkers such as multivalent metal salts may also be employed. Mixtures of the crosslinking agents mentioned can also be employed. The content of the internal crosslinking agents is from about 0.01% to about 5% by weight, such as from about 0.2% to about 3% by weight, based on the total amount of the polymerizable unsaturated acid-group-containing-monomer.

In some aspects, initiators can be used for initiation of the free-radical polymerization. Suitable initiators include, but are not limited to, azo or peroxo compounds, redox systems or UV initiators, sensitizers, and/or radiation.

After polymerization, the superabsorbent polymer is generally formed into particles. In some aspects, the SAP particles may then be surface crosslinked after polymerization by the addition of a surface crosslinking agent and heat-treatment. In general, surface crosslinking is a process that is believed to increase the crosslink density of the polymer matrix in the vicinity of the SAP particle surface with respect to the crosslinking density of the particle interior.

In some particular aspects, desirable surface crosslinking agents include chemicals with one or more functional groups that are reactive toward pendant groups of the polymer chains, typically the acid groups. The surface crosslinking agent may be present in an amount of from about 0.001% to about 5% by weight of the dry superabsorbent polymer composition, such as from about 0.01% to about 3% by weight, or from about 0.1% to about 1% by weight, based on the weight of the dry superabsorbent polymer composition. A heat treatment step is desirable after addition of the surface crosslinking agent.

In one particular aspect, the SAP particles are coated or surface-treated with an alkylene carbonate followed by heating to affect surface crosslinking, which can improve the surface crosslinking density and the gel strength characteristics of the SAP particles. More specifically, the surface crosslinking agent is coated onto the SAP particles by mixing the SAP particles with an aqueous alcoholic solution of the alkylene carbonate surface crosslinking agent. The amount of alcohol is determined by the solubility of the alkylene carbonate and is kept as low as possible for various reasons, for instance, protection against explosions. Suitable alcohols are methanol, isopropanol, ethanol, butanol, or butyl glycol, as well as mixtures of these alcohols. In some aspects, the solvent desirably is water, which typically is used in an amount of about 0.3% by weight to about 5.0% by weight, based on the weight of the dry superabsorbent polymer. In other aspects, the alkylene carbonate surface crosslinking agent is dissolved in water without any alcohol. In still other aspects, the alkylene carbonate surface crosslinking agent may be applied from a powder mixture, for example, with an inorganic carrier material, such as silicone dioxide ($SiO_2$), or in a vapor state by sublimation of the alkylene carbonate.

To achieve the desired surface crosslinking properties, the alkylene carbonate is distributed evenly on the particulate superabsorbent polymer. For this purpose, mixing is effected in suitable mixers known in the art, such as fluidized bed mixers, paddle mixers, rotary drum mixers, or twin-worm mixers. It is also possible to carry out the coating of the particulate superabsorbent polymer during one of the process steps in the production of the SAP particles. In one particular aspect, a suitable process for this purpose is the inverse suspension polymerization process.

The heat treatment, which follows the coating treatment, may be carried out as follows. In general, the heat treatment can occur at a temperature of from about 100° C. to about 300° C. Lower temperatures are possible if highly reactive epoxide crosslinking agents are used. However, if alkylene carbonates are used, then the thermal treatment is suitably at a temperature of from about 150° C. to about 250° C. In this particular aspect, the treatment temperature depends on the dwell time and the kind of alkylene carbonate. For example, at a temperature of about 150° C., the thermal treatment is carried out for one hour or longer. In contrast, at a temperature of about 250° C., a few minutes (e.g., from about 0.5 minutes to about 5 minutes) are sufficient to achieve the desired surface cross-linking properties. The thermal treatment may be carried out in conventional dryers or ovens known in the art.

While particles may be used by way of example of the physical form of superabsorbent polymer composition, the invention is not limited to this form and is applicable to other forms such as fibers, foams, films, beads, rods, and the like, as discussed above. In some aspects, when the superabsorbent polymer composition exists as particles or in granule form, it is desirable that these particles have a size of from about 150 cm to about 850 μm based on the sieving process that is well known in the superabsorbent industry.

In some aspects, the superabsorbent polymer composition of the present invention includes from 0% to about 5% by weight, such as from about 0.001% to about 5% by weight, or from about 0.01% to about 0.5% by weight, (based on the dry superabsorbent polymer composition) of a polymeric coating, such as a thermoplastic coating, or a cationic coating, or a combination of a thermoplastic coating and a cationic coating. In some particular aspects, the polymeric coating desirably is a polymer that may be in a solid, emulsion, suspension, colloidal, or solubilized state, or combinations thereof. Polymeric coatings suitable for this invention may include, but are not limited to, a thermoplastic coating having a thermoplastic melt temperature wherein the polymeric coating is applied to the particle surface coincident with or followed by a temperature of the treated superabsorbent polymer particle at about the thermoplastic melt temperature.

Examples of suitable thermoplastic polymers include, but are not limited to, polyolefin, polyethylene, polyester, polyamide, polyurethane, styrene polybutadiene, linear low density polyethylene (LLDPE), ethylene acrylic acid copolymer (EAA), ethylene alkyl methacrylate copolymer (EMA), polypropylene (PP), maleated polypropylene, ethylene vinyl acetate copolymer (EVA), polyester, polyamide, and blends of all families of polyolefins, such as blends of PP, EVA, EMA, EEA, EBA, HDPE, MDPE, LDPE, LLDPE, and/or VLDPE. In some particular aspects, maleated polypropylene is a desirable thermoplastic polymer for use in the present invention. A thermoplastic polymer may be functionalized to have additional benefits such as water solubility or dispersability.

Polymeric coatings of this invention may also include a cationic polymer. A cationic polymer as used herein refers to a polymer or mixture of polymers comprising a functional group or groups having a potential of becoming positively charged ions upon ionization in an aqueous solution. Suitable functional groups for a cationic polymer include, but are not limited to, primary, secondary, or tertiary amino groups, imino groups, imido groups, amido groups, and quaternary ammonium groups. Examples of synthetic cationic polymers include, but are not limited to, the salts or partial salts of poly(vinyl amines), poly(allylamines), poly(ethylene imine), poly(amino propanol vinyl ethers), poly(acrylamidopropyl trimethyl ammonium chloride), and poly(diallyldimethyl ammonium chloride). Poly(vinyl amines) include, but are not limited to, LUPAMIN 9095 available from BASF Corporation, Mount Olive N.J. Examples of natural-based cationic polymers include, but are not limited to, partially deacetylated chitin, chitosan, and chitosan salts. Synthetic polypeptides such as polyasparagins, polylysines, polyglutamines, and polyargeneines are also suitable cationic polymers.

The superabsorbent polymer composition according to the invention may include from about 0.01% to about 2% by weight, such as from about 0.01% to about 1% by weight, based on the dry superabsorbent polymer composition of a water-insoluble inorganic metal compound. The water-insoluble inorganic metal compound may include, but are not limited to, a cation selected from aluminum, titanium, calcium, or iron and an anion selected from phosphate, borate, or chromate. Examples of water-insoluble inorganic metal compounds include aluminum phosphate and/or an insoluble metal borate. The insoluble metal borate is selected from titanium borate, aluminum borate, iron borate, magnesium borate, manganese borate, or calcium borate. The chemical formula "TiBO" will be used herein to designate titanium borate and analogous compounds such as titanium (III) borate $TiBO_3$. In addition, the chemical formulation also designates the case when titanium (III) borate $TiBO_3$ is treated with hydrogen peroxide to obtain titanium (IV) borate. The inorganic metal compound may have a mass median particle size of less than about 2 μm, such as less than about 1 μm.

The inorganic metal compound can be applied in the dry physical form to the surface of the superabsorbent polymer particles. For this, the superabsorbent polymer particles can be intimately mixed with the finely divided inorganic metal compound. The finely divided inorganic metal compound is suitably added at about room temperature to the superabsorbent polymer particles and mixed in until a homogeneous mixture is present. For this purpose, mixing is effected in suitable mixers known in the art, such as fluidized bed mixers, paddle mixers, rotary drum mixers, or twin-worm mixers. The mixing of the superabsorbent polymer particles with the finely divided water-insoluble inorganic metal compound may take place before or after any surface crosslinking, for example during the application of the surface crosslinking agent.

Alternatively, a suspension of a finely divided water-insoluble inorganic metal compounds can be prepared and applied to a particulate water absorbent polymer. The suspension is applied by means known in the art, for example, by spraying. Useful dispersion media for preparing the suspension include water, organic solvents such as alcohols, for example methanol, ethanol, and isopropanol; ketones, for example acetone, and methyl ethyl ketone; or mixtures of water with the aforementioned organic solvents. Other useful dispersion media include dispersion aids, surfactants, protective colloidals, viscosity modifiers, and other auxiliaries to assist in the preparation of the suspension. The suspension can be applied in conventional reaction mixers or mixing and drying systems as described above at a temperature in the range from room temperature to less than the boiling point of the dispersion medium, preferably at about room temperature. It is appropriate to combine the application of the suspension with a surface crosslinking step by dispersing the finely divided water-insoluble metal salt in the solution of the surface crosslinking agent. Alternatively, the suspension can also be applied before or after the surface crosslinking step. In some aspects, the application of the slurry may be followed by a drying step.

In some aspects, the superabsorbent polymer composition according to the present invention can include from 0% to about 5% by weight, such as from about 0.01% to about 3% by weight, of silica, based on the superabsorbent polymer composition. Examples of silica include, but are not limited to, fumed silica, precipitated silica, silicon dioxide, silicic acid, and silicates. In some particular aspects, microscopic noncrystalline silicon dioxide is desirable. In some aspects, the particle diameter of the inorganic powder can be 1,000 µm or smaller, such as 100 cm or smaller.

In some aspects, the superabsorbent polymer composition may also include from 0% to about 30% by weight, such as from about 0.1% to about 5% by weight, of water-soluble polymers, based on the total amount of the superabsorbent polymer composition, such as partly or completely hydrolyzed polyvinyl acetate, polyvinylpyrrolidone, starch or starch derivatives, polyglycols, polyethylene oxides, polypropylene oxides, or polyacrylic acids. In some particular aspects, the water-soluble polymers are desirably in polymerized-in form.

In some aspects, additional surface additives may optionally be employed with the superabsorbent particles, such as odor-binding substances, such as cyclodextrins, zeolites; inorganic or organic salts, and similar materials; anti-caking additives; flow modification agents; surfactants; viscosity modifiers; and the like. In addition, surface additives may be employed that perform several roles during surface modifications. For example, a single additive may be a surfactant, a viscosity modifier, and it may react to crosslink polymer chains.

In some aspects, the superabsorbent polymer composition of the present invention may be, after a heat treatment step, treated with water so that the superabsorbent polymer composition has a water content of up to about 10% by weight of the superabsorbent polymer composition. This water may be added with one or more of the surface additives from above.

The superabsorbent polymer composition according to the invention are desirably prepared continuously or discontinuously in a large-scale industrial manner, the after-crosslinking according to the invention being carried out accordingly. For example, according to one method of preparation, the partially neutralized monomer, such as acrylic acid, is converted into a gel by free-radical polymerization in aqueous solution in the presence of crosslinking agents and any further components, and the gel is comminuted, dried, ground, and sieved off to the desired particle size. This polymerization can be carried out continuously or discontinuously. For the present invention, the size of the high-capacity superabsorbent polymer composition particles is dependent on manufacturing processes including milling and sieving. It is well known to those skilled in the art that particle size distribution of the superabsorbent polymer particles resembles a normal distribution or a bell shaped curve. It is also known that for various reasons, the normal distribution of the particle size distribution may be skewed in either direction.

The superabsorbent polymer composition particles of the present invention generally include particle sizes ranging from about 50 to about 1000 microns, such as from about 150 to about 850 microns. The present invention may include at least about 40 wt % of the particles having a particle size from about 300 µm to about 600 µm, such as at least about 50 wt % of the particles having a particle size from about 300 µm to about 600 µm, or at least about 60 wt % of the particles having a particle size from about 300 µm to about 600 µm as measured by screening through a U.S. standard 30 mesh screen and retained on a U.S. standard 50 mesh screen. In addition, the size distribution of the superabsorbent polymer composition particles of the present invention may include less than about 30% by weight of particles having a size greater than about 600 microns, and less than about 30% by weight of particles having a size of less than about 300 microns as measured using for example a RO-TAP Mechanical Sieve Shaker Model B available from W. S. Tyler, Inc., having a place of business in Mentor, Ohio, U.S.A.

According to another method of preparation, inverse suspension and emulsion polymerization can also be used for preparation of the superabsorbent polymer composition according to the invention. According to these processes, an aqueous, partly neutralized solution of monomer, such as acrylic acid, is dispersed in a hydrophobic, organic solvent with the aid of protective colloids and/or emulsifiers, and the polymerization is started by free radical initiators. The internal crosslinking agents may be either dissolved in the monomer solution and are metered in together with this, or are added separately and optionally during the polymerization. The addition of a water-soluble polymer as the graft base optionally takes place via the monomer solution or by direct introduction into the organic solvent. The water is then removed azeotropically from the mixture, and the polymer is filtered off and optionally dried. Internal crosslinking can be carried out by polymerizing-in a polyfunctional crosslinking agent dissolved in the monomer solution and/or by reaction of suitable crosslinking agents with functional groups of the polymer during the polymerization steps.

The superabsorbent polymer composition of the present invention exhibits certain characteristics, or properties, as measured by Free Swell Gel Bed Permeability (GBP), Centrifuge Retention Capacity (CRC), and absorbency under load at about 0.9 psi (AUL(0.9 psi)). The Free Swell Gel Bed Permeability (GBP) Test is a measurement of the permeability of a swollen bed of superabsorbent material (in Darcy) under a confining pressure after what is commonly referred to as "free swell" conditions. In this context, the term "free swell" means that the superabsorbent material is allowed to swell without a swell restraining load upon absorbing saline test solution as described above.

The Centrifuge Retention Capacity (CRC) Test measures the ability of the superabsorbent composition to retain liquid therein after being saturated and subjected to centrifugation under controlled conditions. The resultant retention capacity is stated as grams of liquid retained per gram weight of the sample (g/g).

In some aspects, the superabsorbent polymer compositions according to the invention show a significant improvement in permeability, i.e. an improvement in the transportation of liquid in the swollen state, while maintaining high absorption and retention capacity, as compared to known superabsorbent polymer compositions.

In other aspects, the superabsorbent polymer composition of the present invention exhibits a significant improvement in retention capacity (i.e., an improvement in the volume of liquid that the superabsorbent polymer composition can absorb) while maintaining high permeability, as compared to known superabsorbent polymer compositions.

The superabsorbent polymer compositions according to the invention can be employed in many products including sanitary towels, diapers, or wound coverings, and they have the property that they rapidly absorb large amounts of menstrual blood, urine, or other body fluids. Since the agents according to the invention retain the absorbed liquids even under pressure and are also capable of distributing further liquid within the construction in the swollen state, they are more desirably employed in higher concentrations, with respect to other absorbent core components, such as fluff, when compared to conventional current superabsorbent compositions. They are also suitable for use as a homogeneous superabsorber layer without fluff content within an absorbent article construction, as a result of which particularly thin articles are possible.

The preparation of laminates in the broadest sense, and of extruded and coextruded, wet- and dry-bonded, as well as subsequently bonded structures, are possible as further preparation processes. A combination of these possible processes with one another is also possible.

The superabsorbent polymer compositions according to the invention may also be employed in absorbent articles that are suitable for further uses. In particular, the superabsorbent polymer compositions of this invention can be used in personal care absorbent articles, health/medical absorbent articles, household/industrial absorbent articles, sports/construction absorbent articles, and the like.

Figure 12A:
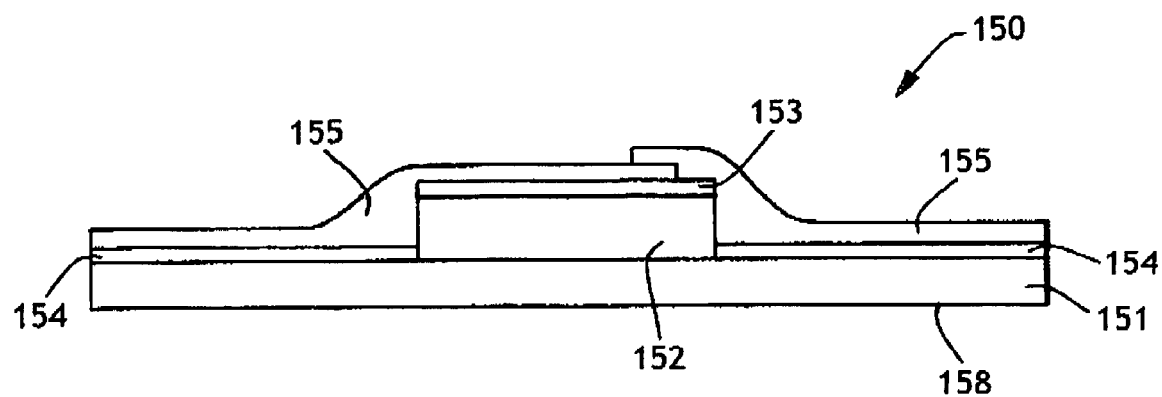
FIG. 12A is a cross-section side view of an absorbent bandage of the present invention.
Figure 12B:
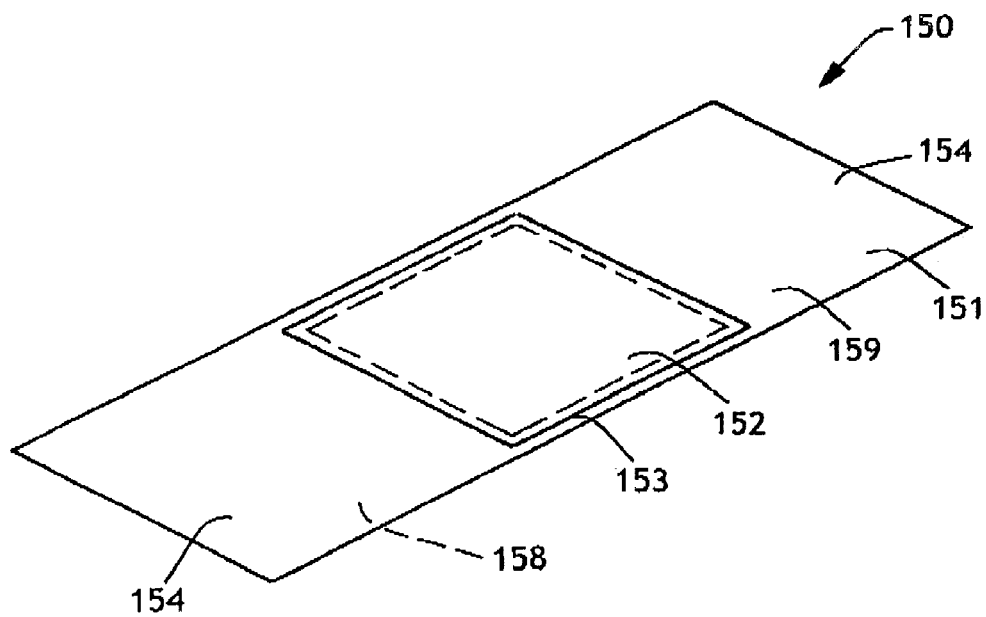
FIG. 12B is a top perspective view of an absorbent bandage of the present invention.

In addition to the absorbent article described above, the present invention may be exemplified as an absorbent bandage. Attention is directed to FIGS. 12A and 12B, which show a possible configuration for a bandage of the present invention. FIG. 12A shows a cross-section view of the absorbent bandage with optional layers described below. FIG. 12B shows a perspective view of the bandage of the present invention with some of the optional or removable layers not being shown. The absorbent bandage 150 has a strip 151 of material having a body-facing side 159 and a second side 158 which is opposite the body-facing side. The strip is essentially a backsheet and is desirably prepared from the same materials described above for the backsheet. In addition, the strip may be an apertured material, such as an apertured film, or material which is otherwise gas permeable, such as a gas permeable film. The strip 151 supports an absorbent core 152 comprising the superabsorbent polymer composition of the present invention which is attached to the body-facing side 159 of the strip. In addition, an absorbent protective layer 153 may be applied to the absorbent core 152 and can be coextensive with the strip 151.

The absorbent bandage 150 of the present invention may also have a pressure sensitive adhesive 154 applied to the body-facing side 159 of the strip 151. Any pressure sensitive adhesive may be used, provided that the pressure sensitive adhesive does not irritate the skin of the user. Suitably, the pressure sensitive adhesive is a conventional pressure sensitive adhesive which is currently used on similar conventional bandages. This pressure sensitive adhesive is desirably not placed on the absorbent core 152 or on the absorbent protective layer 153 in the area of the absorbent core 152. If the absorbent protective layer is coextensive with the strip 151, then the adhesive may be applied to areas of the absorbent protective layer 153 where the absorbent core 152 is not located. By having the pressure sensitive adhesive on the strip 151, the bandage is allowed to be secured to the skin of a user in need of the bandage. To protect the pressure sensitive adhesive and the absorbent, a release strip 155 can be placed on the body-facing side 159 of the bandage. The release liner may be removably secured to the article attachment adhesive and serves to prevent premature contamination of the adhesive before the absorbent article is secured to, for example, the skin. The release liner may be placed on the body-facing side of the bandage in a single piece (not shown) or in multiple pieces, as is shown in FIG. 12A.

In another aspect of the present invention, the absorbent core of the bandage may be placed between a folded strip. If this method is used to form the bandage, the strip is suitably fluid permeable.

Figure 13:
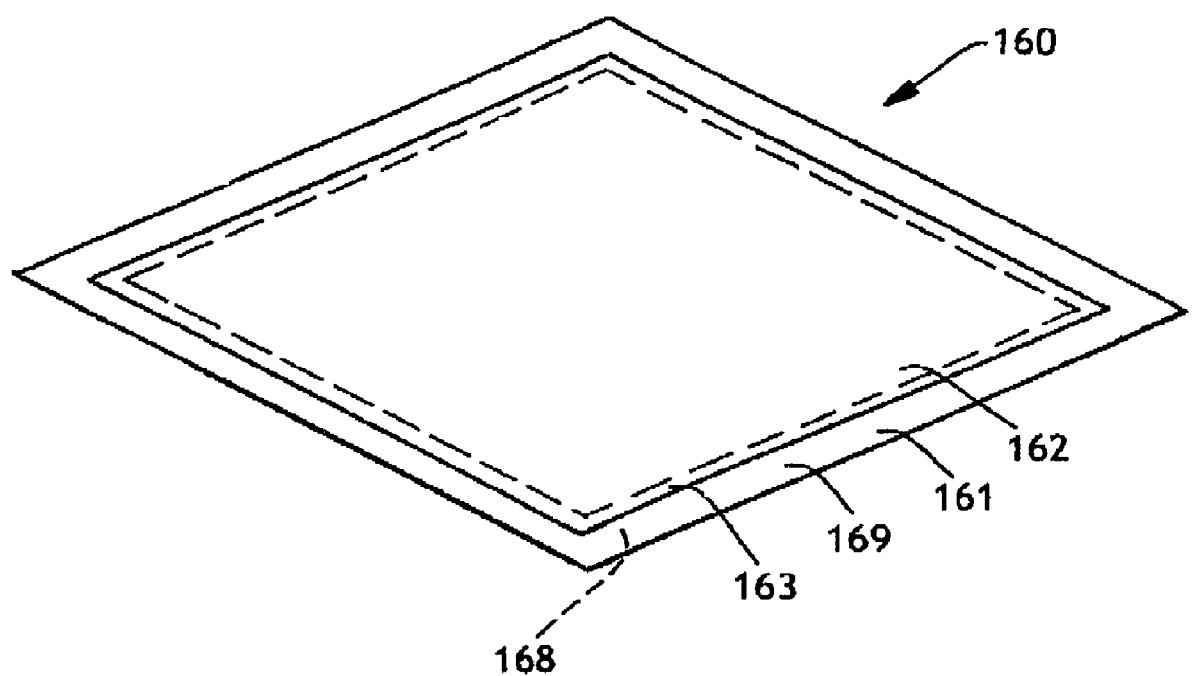
FIG. 13 is a top perspective view of an absorbent bed or furniture liner of the present invention.

Absorbent furniture and/or bed pads or liners are also included within the present invention. As is shown in FIG. 13, a furniture or bed pad or liner 160 (hereinafter referred to as a "pad") is shown in perspective. The pad 160 has a fluid impermeable backsheet 161 having a furniture-facing side or surface 168 and an upward facing side or surface 169 which is opposite the furniture-facing side or surface 168. The fluid impermeable backsheet 161 supports the absorbent core 162 which comprises the superabsorbent polymer composition of the present invention, and which is attached to the upward facing side 169 of the fluid impermeable backsheet. In addition, an optional absorbent protective layer 163 may be applied to the absorbent core. The optional substrate layer of the absorbent core can be the fluid impermeable layer 161 or the absorbent protective layer 163 of the pad.

To hold the pad in place, the furniture-facing side 168 of the pad may contain a pressure sensitive adhesive, a high friction coating or other suitable material which will aid in keeping the pad in place during use. The pad of the present invention can be used in a wide variety of applications including placement on chairs, sofas, beds, car seats and the like to absorb any fluid which may come into contact with the pad.

Figure 14:
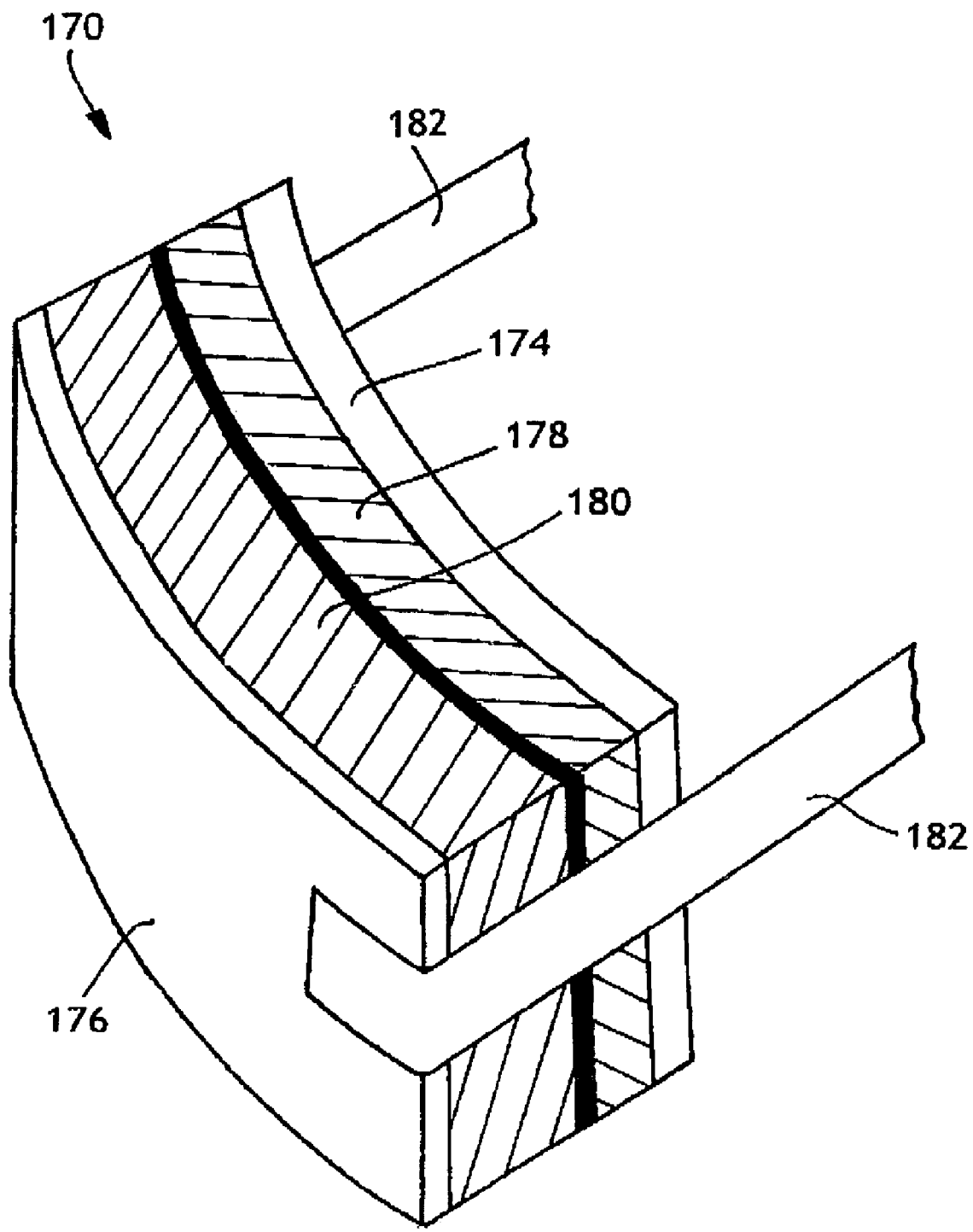
FIG. 14 is a perspective view of an absorbent sweatband of the present invention.

Sports or construction accessories, such as an absorbent headband for absorbing perspiration or drying off equipment are also included within the present invention. As is shown in FIG. 14, an absorbent sweatband 170 is shown in perspective. The sweatband 170 has an absorbent core 180 disposed between an optional topsheet 174 and/or an optional fluid impervious backsheet 176. The absorbent core 180 comprises the superabsorbent polymer composition of the present invention, and in some aspects can include an optional additional region 178 (such as a distribution layer), if desired. The sweatband can be useful to intercept perspiration prior to contact with the hands or eyes. VELCRO or other fastening device 182 can be used to facilitate adjustment or comfort.

The present invention may be better understood with reference to the following examples.

EXAMPLES

Preproduct Fines

Into a polyethylene vessel equipped with an agitator and cooling coils was added, 25.0 kg of 50% NaOH to 37 kg of distilled water and cooled to 20° C. 9.6 kg of glacial acrylic acid was then added to the caustic solution and the solution was again cooled to 20° C. 47.8 g of polyethylene glycol monoallylether acrylate, 47.8 g of ethoxylated trimethylol propane triacrylate SARTOMER 454 product (available from Sartomer Company, having a place of business in Exton, Pa., U.S.A.), and 19.2 kg of glacial acrylic acid were added to the first solution, followed by cooling to 4-6° C. Nitrogen was bubbled through the monomer solution for about 10 minutes. The monomer solution was then discharged in 7.7 kg batches into rectangular trays. To each batch 80 g of 1% by weight of $H_2O_2$ aqueous solution, 120 g of 2 wt % aqueous sodium persulfate solution, and 72 g of 0.5 wt % aqueous sodium erythorbate solution was added homogeneously into the monomer solution stream by injection of the sodium erythorbate solution into the stream of the monomer solution being conveyed from the monomer tank into a tray. The initiated monomer was allowed to polymerize for 20 minutes prior to drying at 175° C. and then grinding. The product was sieved with a MINOX MTS 600DS3V to remove particles smaller than 150 microns. The particles that are smaller than 150 microns are designated as Preproduct Fines.

Preproduct A

Into a polyethylene vessel equipped with an agitator and cooling coils was added 25.0 kg of 50% NaOH to 37 kg of distilled water and cooled to 20° C. 9.6 kg of glacial acrylic acid was then added to the caustic solution and the solution again cooled to 20° C. 47.8 g of polyethylene glycol monoallylether acrylate, 47.8 g of ethoxylated trimethylol propane triacrylate SARTOMER 454 product, and 19.2 kg of glacial acrylic acid were added, followed by cooling to 4-6° C., to form a monomer solution. Nitrogen was bubbled through the monomer solution for about 10 minutes, followed by the addition of 1.88 kg of Preproduct Fines. The monomer solution was then discharged in 7.7 kg batches into rectangular trays. To each batch, as it was being discharged from the vessel into the tray, 80 g of 1% by weight of $H_2O_2$ aqueous solution, 120 g of 2 wt % aqueous sodium persulfate solution, and 72 g of 0.5 wt % aqueous sodium erythorbate solution were added homogeneously into the monomer solution stream by injection of the sodium erythorbate solution into the stream of the monomer solution being conveyed from the monomer vessel into each tray. The initiated monomer was allowed to polymerize for 20 minutes prior to drying at 175° C. and then grinding. The product was sieved with a MINOX MTS 600DS3V to remove particles greater than 850 microns and smaller than 150 microns.

Preproduct $AlPO_4$ Coating Slurry 1269 g of aluminum sulfate tetradecahydrate were dissolved in 1500 g deionized water. The water was in the temperature range of about 85° C. to about 95° C. 860 g of trisodium phosphate was dissolved in 1200 g of hot deionized water. The aluminum sulfate solution was then rapidly poured into the trisodiumphosphate solution. The resulting slurry was rapidly blended with 10 g PLURONIC 25R2 surfactant (available from BASF Corporation, having a place of business in Florham Park, N.J., U.S.A.), and sufficient 50% NaOH was added to bring the pH to neutral (i.e., pH of 7). 1413 g of pure ethylene carbonate was added to the solution to bring the net weight to 6.14 kg. The liquid slurry was filtered through a 100 mesh screen to remove any large particles prior to spraying onto Preproduct A.

$AlPO_4$ Presscake 1269 g of aluminum sulfate tetradecahydrate were dissolved in 1500 g deionized water. The water was in the temperature range of about 85° C. to about 95° C. 860 g of trisodium phosphate was dissolved in 1200 g of deionized water. The water was in the temperature range of about 85° C. to about 95° C. The aluminum sulfate solution was then rapidly poured into the trisodiumphosphate solution. The resulting slurry was rapidly blended with 10 g PLURONIC 25R2 surfactant, and sufficient 50% NaOH was added to bring the pH to neutral (i.e., pH of 7). After precipitation of the $AlPO_4$, the suspension was filtered in a Büchner funnel and the resulting cake was washed with three 500 ml additions of deionized water. The presscake was measured as 20 wt % solids by oven drying.

Titanium Borate Presscake 200 g of disodium tetraborate was dissolved in 800 ml of deionized water. The water was in the temperature range of about 85° C. to about 95° C. 150 g of 45% titanium III sulfate was added to the above solution to form a dark slurry. 35% $H_2O_2$ was added drop-wise to the slurry until a homogenous yellow suspension resulted. The product was filtered in a Büchner funnel, and the cake was washed with deionized water. Solids were determined to be 19.8% by oven drying.

Comparative Examples 1 & 2 and Examples 1-7

Preproduct A (described above) was coated with 1 wt % ethylene carbonate and 4 wt % water using a 20 wt % aqueous solution. The coated Preproduct A was fed at a rate of 60-70 grams/minute into a continuous paddle reactor with a peak temperature of 215° C. and a residence time of about 50 minutes to accomplish surface crosslinking of the particulate polymer. The surface crosslinked particulate material was then post treated with various Surface Treatments as set forth in Table 1 below. The material was then tested for Centrifuge Retention Capacity (CRC), Free Swell Gel Bed Permeability (Free Swell (0 psi) GBP), and Absorbency Under Load at 0.9 psi (AUL (0.9 psi)), the results of which can be seen in Table 1 below.

TABLE 1

Comparative Examples 1 & 2 and Examples 1-8

|  | Surface Treatment[1] | CRC (g/g) | Free swell (0 psi) GBP, (Darcy) | AUL (0.9 psi) (g/g) |
|---|---|---|---|---|
| Comparative Example 1 | 5 wt % of a 1.6 wt % aqueous solution of PEG 8000 | 34.7 | 3 | 16.4 |
| Comparative Example 2 | 5 wt % water and then 0.5 wt % SIPERNAT 22S silica | 34.8 | 7 | 14.4 |
| Example 1 | 5.5 wt % of a 9.09 wt % $AlPO_4$ slurry (prepared from 2.5 parts $AlPO_4$ press cake and 3 parts water) to deliver 0.5% $AlPO_4$ and 5% water | 35.1 | 19 | 17.8 |
| Example 2 | 5.25 wt % of a 4.76 wt % $AlPO_4$ slurry (prepared from 1.25 parts $AlPO_4$ press cake and 4.25 parts water) to deliver 0.25 wt % $AlPO_4$ | 34.8 | 19 | 18.4 |

TABLE 1-continued

Comparative Examples 1 & 2 and Examples 1-8

| | Surface Treatment[1] | CRC (g/g) | Free swell (0 psi) GBP, (Darcy) | AUL (0.9 psi) (g/g) |
|---|---|---|---|---|
| Example 3 | and 5 wt % water<br>5.025 wt % of a 0.498 wt % AlPO$_4$ slurry (prepared from 0.125 parts AlPO$_4$ press cake, 2.5 parts 10% aqueous LUPAMIN 9095, and 2.4 parts water) to deliver 0.025 wt % AlPO$_4$, 0.25 wt % LUPAMIN 9095, and 4.75 wt % water | 35.5 | 17 | 16.0 |
| Example 4 | 5.25 wt % of a 4.76 wt % AlPO$_4$ slurry (prepared from 1.25 parts AlPO$_4$ press cake, 2.5 parts 10% aqueous LUPAMIN 9095, and 1.75 parts water) to deliver 0.25 wt % AlPO$_4$, 0.25 wt % LUPAMIN 9095, and 4.75 wt % water | 34.8 | 22 | 17.3 |
| Example 5 | 5.5 wt % 9.09 wt % TiBO slurry (prepared from 2.52 parts TiBO press cake and 2.97 parts water) to deliver 0.5% TiBO and 5% water | 35.1 | 24 | 16.0 |
| Example 6 | 5.25 wt % of a 4.76 wt % TiBO slurry (prepared from 1.26 parts TiBO press cake and 4.24 parts water) to deliver 0.25 wt % TiBO and 5 wt % water | 35.1 | 19 | 18.0 |
| Example 7 | 5.025 wt % of a 0.498 wt % TiBO slurry (prepared from 0.126 parts TiBO press cake, 2.5 parts 10% aqueous LUPAMIN 9095, and 2.4 parts water) to deliver 0.025 wt % TiBO, 0.25 wt % LUPAMIN 9095, and 4.75 wt % water | 35 | 13 | 15.5 |

[1]Post-treatment component added in combination with 5% wt water of preproduct.
[2]LUPAMIN 9095 aqueous solution of polyvinyl amine.

Example 8

A blend of 2.5 parts of AlPO$_4$ presscake, 1 part ethylene carbonate and 2 parts water was prepared. The blend was sprayed onto 100 parts of Preproduct A with an air atomizer nozzle. The coated Preproduct A was fed at a rate of 60-70 grams/minute into a continuous paddle reactor with a peak temperature of 215° C. and a residence time of about 50 minutes to accomplish surface crosslinking of the particulate polymer. The surface crosslinked particulate material was then post treated with 2 wt % of a 10 wt % LUPAMIN 9095 aqueous solution. The properties of Example 8 compared with a conventional superabsorbent polymer composition are set forth in Table 2 below.

TABLE 2

| | Example 8 | | |
|---|---|---|---|
| Example | CRC (g/g) | Free swell (0 psi) GBP, (Darcy) | AUL (0.9 psi) (g/g) |
| FAVOR SXM 9300[1] | 31 | 41 | 16 |
| Example 8 | 34.4 | 51 | 16.2 |

[1]FAVOR SXM 9300 is available from Stockhausen Inc., having a place of business in Greensboro, North Carolina, U.S.A.

It can be seen from Table 2 that the polymer composition of the present invention exhibits an improved centrifuge retention capacity (CRC), an improved free swell gel bed permeability (FSGBP) while maintaining a similar absorbency under load when compared to a conventional superabsorbent polymer composition.

Preproduct B

In an insulated, flat-bottomed reaction vessel, 1866.7 g of 50 wt % NaOH was added to 3090.26 g of distilled water and cooled to 25° C. 800 g of acrylic acid was then added to the caustic solution and the solution again cooled to 25° C. A second solution of 1600 g of acrylic acid containing 120 g of 50% by weight methoxypolyethyleneglycol monomethacrylate in acrylic acid and 14.4 g of ethoxylated trimethylolpropanetriacrylate was then added to the solution, followed by cooling to 5° C., all while stirring, to form a monomer solution. The monomer solution was then polymerized with a mixture of 100 ppm hydrogen peroxide, 200 ppm azo-bis-(2-amidino-propene)dihydrochloride, 200 ppm sodium persulfate, and 40 ppm ascorbic acid (all aqueous solutions) under adiabatic conditions and held near the maximum temperature ($T_{max}$) for 25 minutes. The resulting gel was chopped and extruded with a HOBART 4M6 commercial extruder, followed by drying in a PROCTER & SCHWARTZ Model 062 forced air oven at 175° C. for 10 minutes with up flow and 6 minutes with down flow air on a 20 in×40 in (51 cm×102 cm) perforated metal tray to a final product moisture level of less than 5 wt %. The dried material was coarse-ground in a PRODEVA Model 315-S crusher, milled in an MPI 666-F three-stage roller mill and sieved with an MINOX MTS 600DS3V to remove particles greater than 850 μm and smaller than 150 μm.

Example 9

Preproduct B was coated in an ANVIL MIX9180 mixer with 1% ethylene carbonate, 4% water, 0.5% Preproduct $AlPO_4$ Slurry as described above, 350 ppm maleated polypropylene, and 0.2% SIPERNAT S22S silica based on the dry superabsorbent polymer weight. The coated superabsorbent polymer was heat treated to about 205° C. for about 45-50 minutes residence time in order to effectuate the surface crosslinking of the polymer particles.

After surface crosslinking the resulting particles were cooled to room temperature and then were post-treated by spraying the particles with 2 wt % of a solution prepared from 5 parts of LUPAMIN 9095 polyvinyl amine solution and 95 parts water in a kitchen type mixer with a wire wisk. The resultant product was allowed to equilibrate for at least 2 hours, and then sieved through U.S. standard #20 mesh and retained on U.S. standard #100 mesh. The resulting superabsorbent polymer composition was then tested for CRC and Free Swell GBP, the results of which can be seen in Table 3 below.

TABLE 3

Example 9

| Example | Metal Compound | Polymeric Coating | CRC g/g | Free swell (0 psi) GBP, Darcy |
|---|---|---|---|---|
| FAVOR SXM 9300 | — | — | 31 | 41 |
| Example 9 | 0.5% $AlPO_4$ | 350 ppm MPP[2] 2 wt % of 5 wt % LUPAMIN 9095[1] | 33.1 | 42 |

[1]LUPAMIN 9095 polyvinyl amine solution
[2]Maleated Polypropylene

It can be seen from Table 3 that the polymer composition of the present invention exhibits an improved centrifuge retention capacity (CRC), while maintaining a similar free swell gel bed permeability (FSGBP) when compared to a conventional superabsorbent polymer composition.

In addition, the foregoing example was sieved for 10 minutes using a RO-TAP Mechanical Sieve Shaker Model B (available from W. S. Tyler, Inc., having a place of business in Mentor, Ohio, U.S.A.) and found to have the following particle size distribution as set forth in Table 4 below.

TABLE 4

Example 9 Particle Size Distribution

| Particle Size | Average % |
|---|---|
| % on 20 mesh (>850 μm) | 0.22 |
| % on 30 mesh (600-850 μm) | 20.79 |
| % on 50 mesh (300-600 μm) | 63.35 |
| % on 170 mesh (45-90 μm) | 15.6 |
| % on 325 mesh (45-90 μm) | 0.04 |
| % on 325 mesh (<45 μm) | 0 |

Example 10

Preproduct B was continuously coated in a Shugi mixer with 3% by weight of preproduct of a 33% aqueous ethylene carbonate solution, 2.5% by weight of preproduct of a 20% aluminum phosphate slurry, and 0.2% by weight of preproduct of SIPERNAT S22S. The aluminum phosphate slurry was blended with CHEMCOR 43G40SP maleated polypropylene (MPP) to deliver 350 ppm MPP in the aluminum phosphate spray. Coated Preproduct B was then fed into a continuous paddle reactor for a residence time of about 30 minutes and a peak superabsorbent temperature of about 199° C. The resulting surface-crosslinked superabsorbent polymer particles were then cooled and post-treated with 2% of a solution prepared from 5 parts LUPAMIN polyvinyl amine solution and 95 parts water in an ANVIL Model Number MIX9180 kitchen type mixer with a wire wisk. After post-treatment, superabsorbent polymer particles were allowed to stand for at least 2 hours prior to sieving through a U.S. standard #20 mesh and retained on U.S. standard #100 mesh screen. The resulting superabsorbent polymer composition particles were then tested for CRC, Free Swell GBP and AUL, the results of which appear in Table 5 below.

TABLE 5

Example 10

| Example | CRC (g/g) | Free swell (0 psi) GBP, (Darcy) | AUL (0.9 psi) (g/g) |
|---|---|---|---|
| FAVOR SXM 9300 | 31 | 41 | 16 |
| Example 10 | 33.2 | 47 | 16.6 |

It can be seen from Table 5 that the polymer composition of the present invention exhibits an improved centrifuge retention capacity (CRC), an improved free swell gel bed permeability (FSGBP) while maintaining a similar absorbency under load when compared to a conventional superabsorbent polymer composition.

Example 11

Absorbent Core

Handsheets were prepared using standard airforming handsheet equipment to yield a 10 inch by 17 inch (25 cm×43 cm) composite handsheet. A total of about 36.19 grams of FAVOR SXM 9300 (available from Stockhausen Inc., having a place of business in Greensboro, N.C., U.S.A.) and about 24.13 grams of Weyerhaeuser NB480 fluff fiber were first used to create comparative (control) sample composites, each with a target basis weight of 550 grams per square meter (GSM). Then, a total of about 32.90 grams of the superabsorbent polymer composition of Example 8 described above and about 21.94 grams of Weyerhaeuser NB480 fluff fiber were used to create each sample of the invention having a target basis weight of 500 grams per square meter (GSM). A forming tissue with a basis weight of about 16.6 gsm (White Wrap Sheet, available from Cellu Tissue Holdings, Inc., a business having offices located in East Hartford, Conn., U.S.A.) was used for the top and bottom of each sample. A sheet of the forming tissue was placed on the bottom of the former. Then, the superabsorbent material and the NB480 were each divided into about equal portions (i.e. 6 portions of fluff and 5 portions of superabsorbent materials). Each fluff portion and superabsorbent polymer portion was alternatively introduced into the top of the former, allowing the vacuum to disperse the fluff and superabsorbent materials into the former chamber and onto the forming tissue. This process was continued until the last portion of fluff was consumed, forming a substantially uniform distribution of fluff and superabsorbent materials. Another sheet of forming tissue was then placed on top of the sample, and the sample was densified to approximately 0.28 g/cc. A suitable device for densification is a carver press, such as CARVER PRESS model #4531 (available from Carver, Inc., a business having offices located in Wabash, Ind., U.S.A.). Samples were then cut from the composite handsheets in appropriate sizes for testing, as set forth in the test procedures described above. The samples were tested for Saturated Capacity (SAT CAP) and Fluid Intake Rate (FIR) as described in the test procedures above. The results can be seen in Table 6 below.

TABLE 6

| | Absorbent Composite | |
|---|---|---|
| SAP | 0.5 psi Saturated Capacity (g/g) | $2^{nd}$ Insult Intake Rate (ml/sec) |
| FAVOR SXM 9300 (comparative example) | 20.2 | 1.06 |
| Example 8 | 22.2 | 1.06 |

Table 6 demonstrates that composites containing superabsorbent polymer compositions of the present invention result in an increased saturated capacity (relative to the comparative example) and a 2nd insult intake rate similar to the comparative example, even at a 10% lower basis weight than the comparative example.

Example 12

Absorbent Article

Absorbent articles were prepared utilizing the superabsorbent polymer composition of Example 10 above. Comparative articles (controls) were also prepared utilizing FAVOR SXM 9300 commercial superabsorbent. Each article was identical in construction, except for the type and/or amount of superabsorbent polymer. Each article included a topsheet, a surge layer, an absorbent core comprising superabsorbent polymer composition described below in Table 7, a wrap sheet and a backsheet. The type and amount of each superabsorbent in the articles can be seen in Table 7 below.

TABLE 7

| Article Code | Superabsorbent Type | Superabsorbent Amount per Article (grams) |
|---|---|---|
| Control | FAVOR SXM 9300 | 11.7 |
| Equal Add-on | Superabsorbent Polymer Composition from Example 10 | 11.7 |
| Reduced Add-on | Superabsorbent Polymer Composition from Example 10 | 10.7 |

A Home Use Test was then conducted using the articles. The articles were worn by 382 panelists (190 females, 192 males) who used them under normal use conditions. Subjects tested each code for 3 days of normal use, using approximately 4 products per day.

A diary sheet, with pre-written questions, was provided for all individual products on which a care giver of the panelists recorded information pertaining to leakage. All used products were returned and weighed to determine the amount of urine they contained. One aspect of particular interest for articles was the amount of fluid the product contained before it failed (leak). In normal use this will be difficult to observe directly as the majority of products will be changed before they have failed. The products that do fail provide an exact measure of the capacity at failure (when the product is removed), while the products that were removed before failure provide a lower bound on the capacity at failure of that article. These two types of information can be combined, as taught in the statistical methodology known as reliability, or survival analysis, to estimate the probability of failure at any given dose. A common summary of these failure curves is the median load (dose) at leakage, also known as the LD50. Since these failure curves are usually skewed to the right, a median is a more commonly used summary than is the mean. In the common case where the shape parameter of the curve is the same for all products being compared, it is sufficient to compare the LD50 values to order the products according to capacity at failure.

Results from the diary sheets and the survival analysis for the returned articles from this home use test, segregated by gender, are indicated in Table 8 and Table 9 below:

TABLE 8

| Article Description | LD50 (g) (for Boy users) | % Product Leaks (for Boy users) |
|---|---|---|
| FAVOR SXM 9300 at 11.7 g | 354 | 10.4 |
| Superabsorbent Polymer Composition of Example 10 at 11.7 g | 369 | 9.2 |
| Superabsorbent Polymer Composition of Example 10 at 10.7 g | 351 | 10.6 |

TABLE 9

| Article Description | LD50 (g) (for Girl users) | % Product Leaks (for Girl users) |
|---|---|---|
| FAVOR SXM 9300 at 11.7 g | 344 | 9.1 |
| Superabsorbent Polymer Composition of Example 10 at 11.7 g | 357 | 8.5 |
| Superabsorbent Polymer Composition of Example 10 at 10.7 g | 344 | 10.8 |

As can be seen from the data in Tables 8 and 9, the articles which contain the superabsorbent polymer composition from Example 10 have similar leakage behavior as articles containing a commercially available superabsorbent polymer, even when the products with the Example 10 superabsorbent polymer composition have less (by weight) superabsorbent per product.

It will be appreciated that details of the foregoing examples, given for purposes of illustration, are not to be construed as limiting the scope of this invention. Although only a few exemplary embodiments of this invention have been described in detail above, those skilled in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the desirable embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

What is claimed is:

1. An absorbent article comprising an absorbent core;
   wherein the absorbent core includes a superabsorbent polymer composition comprising a superabsorbent polymer and a surface additive;
   wherein the superabsorbent polymer comprises:
   a) from about 55% to about 99.9% by weight of a polymerizable unsaturated acid-group-containing-monomer based on the superabsorbent polymer; and
   b) from about 0.001% to about 5% by weight of internal crosslinking agent based on the polymerizable unsaturated acid-group-containing-monomer;
   wherein the superabsorbent polymer has a degree of neutralization of greater than about 25%;
   wherein elements a) and b) have been polymerized and prepared into superabsorbent polymer particles; and
   wherein the surface additive comprises:
   i) from about 0.001% to about 5% by weight of surface crosslinking agent based on the superabsorbent polymer composition;
   ii) from about 0.01% to about 2% by weight of a water-insoluble inorganic metal compound based on the superabsorbent polymer composition; and
   iii) from 0% to about 5% by weight of a polymeric coating based on the superabsorbent polymer composition.

2. The absorbent article of claim 1 further comprising a topsheet and a backsheet, wherein the absorbent core is disposed between the topsheet and the backsheet.

3. The absorbent article of claim 2 wherein at least one of the topsheet, backsheet, and absorbent core is stretchable.

4. The absorbent article of claim 1 wherein the absorbent core comprises at least about 30% by weight of the superabsorbent polymer composition.

5. The absorbent article of claim 1 wherein the absorbent core comprises about 60% to about 95% by weight of the superabsorbent polymer composition.

6. The absorbent article of claim 1 wherein the absorbent core further comprises fluff.

7. The absorbent article of claim 1 wherein the absorbent core further comprises a surfactant.

8. The absorbent article of claim 1 wherein the absorbent core comprises layers.

9. The absorbent article of claim 8 wherein at least one of the layers comprises substantially only the superabsorbent polymer composition and at least one of the layers comprises substantially only fluff.

10. The absorbent article of claim 1 wherein the article is selected from personal care absorbent articles, health/medical absorbent articles, household/industrial absorbent articles or sports/construction absorbent articles.

11. The absorbent article of claim 1 wherein the superabsorbent polymer composition has been heat-treated.

12. The absorbent article of claim 11 wherein the superabsorbent polymer composition has been heat-treated from about 150° C. to about 250° C.

13. The absorbent article of claim 1 wherein the superabsorbent polymer composition exhibits a centrifuge retention capacity of at least about 30g/g as measured by the Centrifuge Retention Capacity Test and a free swell gel bed permeability of at least about 10 Darcy as measured by the Free Swell Gel Bed Permeability Test.

14. The absorbent article of claim 1 wherein the superabsorbent polymer composition exhibits a centrifuge retention capacity of at least about 32g/g as measured by the Centrifuge Retention Capacity Test, and a free swell gel bed permeability of at least about 20 Darcy as measured by the Free Swell Gel Bed Permeability Test.

15. The absorbent article of claim 1 wherein the superabsorbent polymer composition exhibits a centrifuge retention capacity from about 32g/g to about 40g/g as measured by the Centrifuge Retention Capacity Test, and a free swell gel bed permeability of at least about 40 Darcy as measured by the Free Swell Gel Bed Permeability Test.

16. The absorbent article of claim 1 wherein the water-insoluble inorganic metal compound is selected from a metal phosphate, titanium borate, aluminum borate, iron borate, magnesium borate, manganese borate, and calcium borate.

17. The absorbent article of claim 16 wherein the metal phosphate is aluminum phosphate.

18. The absorbent article of claim 1 wherein particles of the inorganic metal compound have a mass median particle size of less than about 2 μm.

19. The absorbent article of claim 1 wherein the polymeric coating is from about 0.01% to about 0.5% by weight of a thermoplastic polymer based on the superabsorbent polymer composition.

20. The absorbent article of claim 1 wherein the polymeric coating is selected from polyolefin, polyethylene, polyesters, polyurethanes, linear low density polyethylene, ethylene acrylic acid copolymer, styrene copolymers, ethylene alkyl methacrylate copolymer, polypropylene, maleated polypropylene, ethylene vinyl acetate copolymer, polyamide, polyester, or blends and copolymers thereof.

21. The absorbent article of claim 1 wherein the polymeric coating is a cationic polymer.

22. The absorbent article of claim 1 wherein the polymeric coating is a polyvinylamine.

23. The absorbent article of claim 1 wherein the polymeric coating is a blend of maleated polypropylene and ethylene acrylic acid copolymer.

24. The absorbent article of claim 1 wherein at least about 40% by weight of the superabsorbent polymer composition has a particle size from about 300 μm to about 600 μm.

25. The absorbent article of claim 1 wherein at least about 50% by weight of the superabsorbent polymer composition has a particle size from about 300 μm to about 600 μm.

26. The absorbent article of claim 1 wherein at least about 50 wt % of acid groups of the polymerizable unsaturated acid-group-containing-monomer include carboxyl groups;
   wherein the acid groups have been neutralized to at least 50 mol %; and
   wherein the internal crosslinking agent is from about 0.2 wt % to about 3 wt % based on the total amount of the polymerizable unsaturated acid-group-containing-monomer.

27. The absorbent article of claim 1 wherein the water-insoluble inorganic metal compound has been applied to the surface of the superabsorbent polymer particles in suspension form.

28. The absorbent article of claim 1 wherein the water-insoluble, inorganic metal compound has been applied to the surface of the superabsorbent polymer particles in dry form.

29. An absorbent article comprising an absorbent core, wherein the absorbent core includes a superabsorbent polymer composition comprising superabsorbent polymer particles that have been surface treated with from about 0.01 to about 2% by weight of an inorganic metal compound selected from insoluble aluminum phosphate or an insoluble metal borate, based on the superabsorbent polymer composition.

30. The absorbent article of claim 29 further comprising a topsheet and a backsheet, wherein the absorbent core is disposed between the topsheet and the backsheet.

31. The absorbent article of claim 29 wherein at least one of the topsheet, backsheet, and absorbent core is stretchable.

32. The absorbent article of claim 29 wherein the absorbent core comprises at least about 30% by weight of the superabsorbent polymer composition.

33. The absorbent article of claim 29 wherein the absorbent core comprises about 60% to about 95% by weight of the superabsorbent polymer composition.

34. The absorbent article of claim 29 wherein the absorbent core further comprises fluff.

35. The absorbent article of claim 29 wherein the absorbent core further comprises a surfactant.

36. The absorbent article of claim 29 wherein the absorbent core comprises layers.

37. The absorbent article of claim 36 wherein at least one of the layers comprises substantially the superabsorbent polymer composition and at least one of the layers comprises substantially fluff.

38. The absorbent article of claim 29 wherein the article is selected from personal care absorbent articles, health/medical absorbent articles, household/industrial absorbent articles or sports/construction absorbent articles.

39. The absorbent article of claim 29 wherein the superabsorbent polymer composition exhibits a free swell gel bed permeability of at least about 10 Darcy as measured by the Free Swell Gel Bed Permeability Test.

40. The absorbent article of claim 29 wherein the superabsorbent polymer composition exhibits a centrifuge retention capacity of at least about 32 g/g as measured by the Centrifuge Retention Capacity Test, and a free swell gel bed permeability of at least about 20 Darcy as measured by the Free Swell Gel Bed Permeability Test.

41. The absorbent article of claim 29 wherein the insoluble metal borate is selected from titanium borate, aluminum borate, iron borate magnesium borate, manganese borate, and calcium borate.

42. The absorbent article of claim 29 wherein particles of the inorganic metal compound have a median particle size of less than about 2 μm.

43. The absorbent article of claim 29 wherein at least about 40% by weight of the superabsorbent polymer composition has a particle size from about 300 μm to about 600 μm.

44. An absorbent article comprising an absorbent core;
  wherein the absorbent core includes a superabsorbent polymer composition that has been prepared by:
  a) providing superabsorbent polymer particles;
  b) preparing a first solution of a first inorganic metal salt;
  c) preparing a second solution of a second inorganic metal salt; and
  d) applying the first solution and second solution to the superabsorbent polymer particles to form a water-insoluble inorganic metal salt precipitate directly on or in the vicinity of a surface of the superabsorbent polymer particles.

45. The absorbent article of claim 44 further comprising a topsheet and a backsheet, wherein the absorbent core is disposed between the topsheet and the backsheet.

46. The absorbent article of claim 44 wherein the first inorganic metal salt includes a cation selected from aluminum, titanium, calcium or iron and the second inorganic metal salt includes an anion selected from phosphate, borate or chromate.

47. The absorbent article of claim 44 wherein the first inorganic metal salt is aluminum sulfate tetradecahydrate trisodium phosphate and the second inorganic metal salt is trisodium phosphate.

* * * * *